United States Patent [19]

Terstappen

[11] Patent Number: 5,234,816
[45] Date of Patent: Aug. 10, 1993

[54] METHOD FOR THE CLASSIFICATION AND MONITORING OF LEUKEMIAS

[75] Inventor: Leon W. M. M. Terstappen, Palo Alto, Calif.

[73] Assignee: Becton, Dickinson and Company, Franklin Lakes, N.J.

[21] Appl. No.: 731,217

[22] Filed: Jul. 12, 1991

[51] Int. Cl.$^5$ .................. G01N 33/536; G01N 21/64; G01N 33/574

[52] U.S. Cl. ..................... 435/7.24; 436/64; 436/172; 436/536

[58] Field of Search ............... 435/7.24; 436/172, 805, 436/536, 64, 800, 813

[56] References Cited

U.S. PATENT DOCUMENTS 4,987,086  1/1991  Brosnan .............................. 436/501

OTHER PUBLICATIONS

Becton Dickinson Bulletin, Source Book Section 8.2 Mar. 1984 "Leukemia Immunophenotyping Panel".
Terstappen L. Loken M. Myeloid cell differentiation in normal bone marrow and acute myeloid leukemia assessed by multi-dimensional Anal Cell Pathol a:2-29-240, 1990.
L. Terstappen Flow Cytometric analysis of human bone. Leukemia. 1990;4:657-663.
L. Terstappen Flow cytometric assessment of human T Cell. Blood 79:666 1992.
L. Terstappen, et al Identification and Characterization of normal human plasma cells by high resolution flow cytometry. Blood. 1990; 76:1739-1747.
M. Loken et al. Flow cytometric analysis of human bone marrow. Blood 1987; 69:255-263.
M. Loken et al. Flow cytometric analysis of human bone marrow: II. Norman B lymphocyte development. Blood. 1987; 70:1316-1324.
M. Greaves et al. Lineage promiscuity in hematopoietic differentiation and leukemia. Blood. 1986; 67:1-11.
G. Roberts et al. Lineage ambiguity in acyte leukemia. Cancer. 1986; 58:1473-1478.
C. Hurwitz et al. Asynchronous antigen expression in B lineage acute lymphoblastic leukemia. Blood. 1988; 72:299-307.
L. Terstappen et al. Flow Cytometric characterization of acute myeloid leukemia. Part II. Leukemia.; Leukemia 5(9):757 1991.
L. Terstappen et al. Part I. Significance of light scattering properties. Leukemia. Leukemia 5(4):315 1991.
L. Terstappen et al. Quantitative comparison of myeloid antigens of five lineages of mature peripheral blood cells. J Leuk Biol. 1990; 48:138-148.
Bennett, Catovsky D., Daniel M-T. Classification of acute myeloid leukemia Ann Intern Med. 1985; 103:620-624.
Morphologic immunologic,and cytogenic (MIC) working classification of the acute myeloid leukaemias. Brit J Haemat. 1988; 68:487-494.
Foon K., Todd R. Immunologic Classifcation of Leukemia and Lymphoma. Blood 1986; 68:1-31.
Neame P. Soamboonsrup P., Browman G. Classifying acute leukemia by immunophenotyping: Blood. 1986; 68:1355-1362.
Ryan D., Kossover S., Mitchell S., Frantz C. Hennessy L., Cohen H. Subpopulations of common acute lymphoblastic leukemia antigen-positive lymphoid 417-425. Blood 68(2) 1986.

(List continued on next page.)

Primary Examiner—Esther L. Kepplinger
Assistant Examiner—Nancy J. Parsons
Attorney, Agent, or Firm—Robert M. Hallenbeck

[57] ABSTRACT

A method for classifying and monitoring leukemias is disclosed. The method comprises mixing cells from a patient with a plurality of fluorescently labelled monoclonal antibodies, examining the cells by means of flow cytometry, scoring the percent of positive cells in each quadrant in a two-dimensional plot of log fluorescence and comparing the scores with a standard. Monitoring of the disease also may be achieved by comparing the scores before, during and after treatment.

15 Claims, 24 Drawing Sheets

OTHER PUBLICATIONS

V. Shah et al. Quantitative comparison of myeloid antigens on peripheral blood lymphocytes, monocytes, neutrophils, Oxford Univ. Press 1989:855–858 Leukocyte Typing IV 1989.

J. Slockbower et al. Procedures for the collection of diagnostic blood specimens by venipuncture. Villanova Natl. Committee for Clinical Lab Standards, 1984. 4(5):91.

L. Nadler et al. B cell/leukemia panel workshop:- Leukocyte Typing II. New York: Springer-Verlag N.Y. Inc.; 1986: 15–24.

N. Ling et al., B-cell and plasma cell antigens: new and previously defined cluster Leucocyte Typing III. Oxford: Oxford University Press; 1987:302–335.

U. Koller et al. Cluster Report CD33. Leucocyte Typing IV. Oxford: Oxford University Press; 1989:812–813.

L. Terstappen et al. Quantitative comparison of myeloid antigens on five lineage of mature peripheral blood cells, J. Leukocyte Biol. 1990; 48:138–148.

T. LeBien et al. The common acute lymphoblastic leukemia antigen (CD10) Emancipation from a functional enigma. Blood 1989; 73:625–635.

R. Mayer et al. CD5 and immunoglobulin v gene expression in B cell lymphomas and chronic lymphocytic leukemia. Blood. 1990; 75: 1518–1524.

C-H Pui et al. Myeloid-associated antigen expression lacks prognostic value childhood acute lymphoblastic leukemia. Blood. 1990; 75: 198–202.

J. Griffin, The use of monoclonal antibodies in the characterization of myeloid leukemias. Hematol Pathol. 1987; 1:81–91.

B. Dorken et al. B-cell antigens: CD10. Leucocyte Typing IV. Oxford: Oxford University Press; 1989:33–34.

B. Dorken et al. B-cell antigens CD20. Leucocyte Typing IV. Oxford: Oxford University Press; 1989:46–48.

R. Kurrle et al. Cluster report CD3. Leucocyte Typing IV. Oxford:Oxford Univ. Press; 1989:290–293.

L. Lanier et al. Correlation of cell surface antigen expression of human thymocytes by multi-color flow cytometric J. Immunol. 1986; 137:2501–2507.

B. Dorken et al. B-cell antigens: CD19. Leucocyte Typing IV. Oxford: Oxford Univ. Press; 1989: 34–36.

N. Gadol et al. Antigenic phenotype and functional characterization of human tonsil B cells. Blood. 1988; 71:1048–1055.

P. Dorken et al. B-Cell antigens: CD22. Leucocyte Typing IV. Oxford:Oxford Univ. Press; 1989:63–64.

L. Visser et al. Monoclonal antibodies reactive with hairy cell leukemia. Blood. 1989; 74:320–325.

R. Andrews et al. Precursors of colony-forming cells in humans can be distinguished from colony-forming cells etc. J. Exp Med. 1989; 169:1721–1731.

M. Greaves et al. Selective expression of the common acute lymphoblastic leukemia (gp100) antigen on immature etc. Blood, 1983; 61:628–639.

S. Gadd Cluster Report CD13. Leucocyte Typing IV. Oxford: Oxford Univ. Press; 1989: 782–784.

R. Lal. et al. Fixation & Long-term storage of human lymphocytes for surface marker analysis by flow cytometry. Cytometry. 1988; 9:213–219.

L. Hutchin et al. CD20 Cells:B or T? Cytometry. 1990; 109:21.

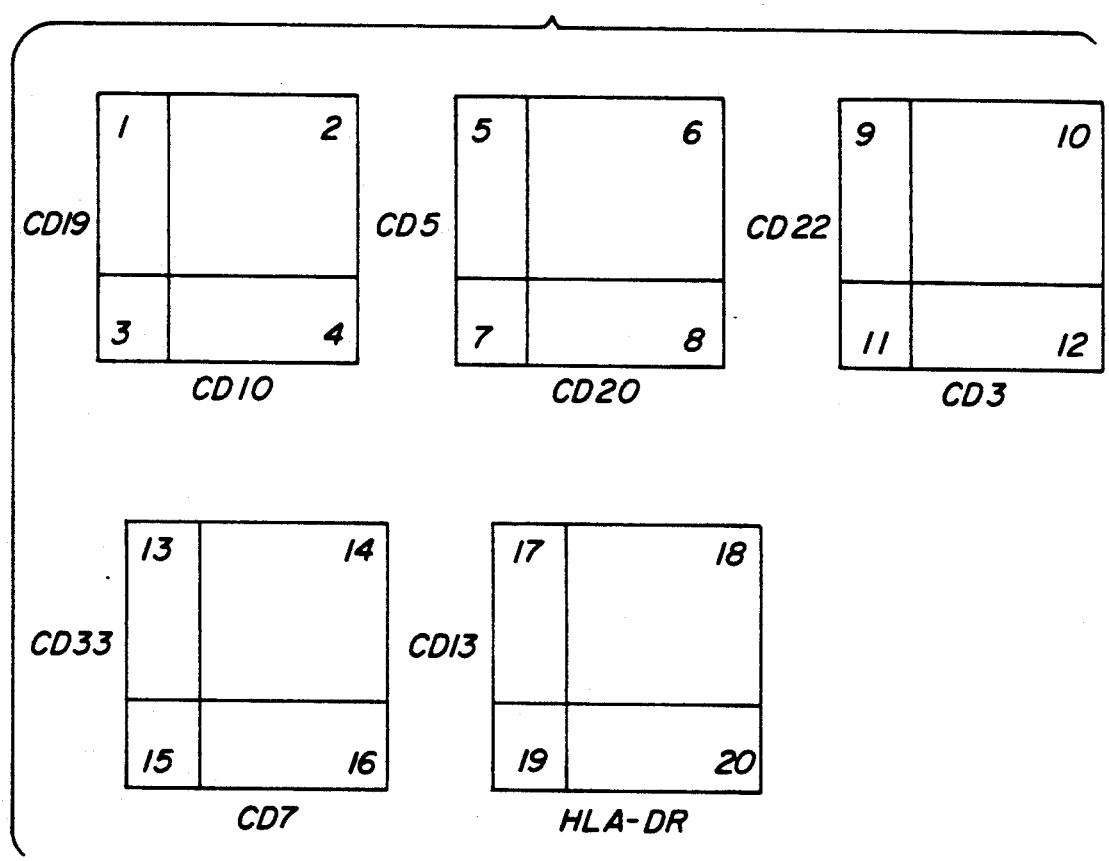

FIG-14
PATIENT IDENTIFICATION:_____
FILE NAME:_____
PHYSICIAN:_____
DATE:_____
QUADRANT NUMBERS ASSIGNED:_____
ABERRANT ANTIGEN EXPRESSION:   ___YES
                               ___NO
COMMENTS:_____
_____
_____
_____
LINEAGE ASSIGNMENT:_____
SIGNATURE:_____
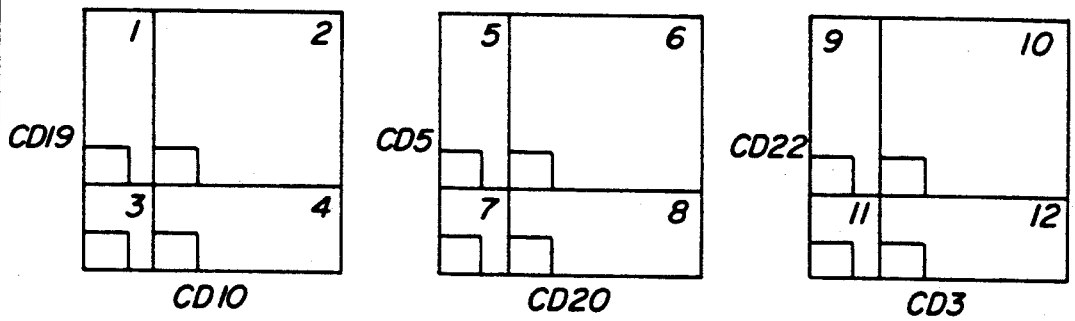
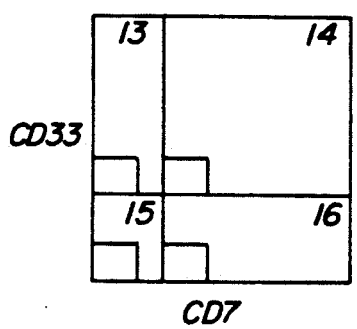
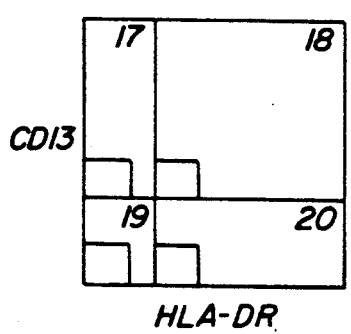

METHOD FOR THE CLASSIFICATION AND MONITORING OF LEUKEMIAS

FIELD OF THE INVENTION

This invention relates to a method for the classification and monitoring of leukemias, and more particularly relates to a method for classification of leukemias wherein a sample of cells from a patient are mixed with a plurality of fluorescently labelled monoclonal antibodies, the cells then are analyzed by means of flow cytometry, the results are scored and the scores are compared with results from a standard.

BACKGROUND OF THE INVENTION

Historically, the most widely accepted classification scheme for acute leukemias has been based on morphological and cytochemical features. This method for classification was proposed by the French-American-British (FAB) group.[1,2] The FAB classification scheme, shown in Table 1, is the primary method used for classification of acute leukemias by visual, microscopic analysis. Accordingly, it remains dependent upon the cell preparation, method of chemical staining and subjectivity of the technician "reading" the slide. More recently, immunophenotyping by flow cytometry has been investigated for assisting in characterizing and subclassifying acute leukemias as B-lymphoid, T-lymphoid, myeloid or undifferentiated.[3,4,5]

In normal bone marrow, unique identification of cell lineage and discrimination between stages of maturation within each cell lineage are possible using flow cytometry.[6,7,8,9,10,11,12] In leukemias, however, cell-surface antigen expression often does not follow the normal maturation pathways, resulting in asynchronous or aberrant expression of cell-surface antigens.[7,13,14,15,16]

TABLE I

| Acute Myeloblastic Leukemia (AML) | | Acute Lymphoblastic Leukemia (ALL) | |
|---|---|---|---|
| M0 | undifferentiated myeloblastic leukemia | L1 | Lymphoblasts, small scanty cytoplasm |
| M1 | Myeloblastic without differentiation | L2 | Heterogeneous, large blast with variable cytoplasm |
| M2 | Myeloblastic with differentiation | L3 | Heterogeneous, large blast with vacuolated cytoplasm |
| M2baso | Myeloblastic with basophilia | | |
| M3 | Hypergranular promyelocytic | | |
| M3v | Microgranular promyelocytic | | |
| M4 | Myelomonocytic | | |
| M4eo | Myelomonocytic with eosinophilia | | |
| M5 | Monocytic (M5a-Monocytic without differentiation) (M5b-Monocytic with differentiation) | | |
| M6 | Erythroleukemia | | |
| M7 | Megakaryoblastic | | |

The aberrant expression of antigens in leukemias complicates the process of characterizing and assigning a lineage to the leukemic cell population.

With respect to the acute leukemias listed in Table I, for example, B-lineage-associated antigens are relatively more specific than the T-lymphoid and myeloid associated antigens, however, T-lymphoid associated antigens have been described on both myeloid and B-lymphoid leukemias.[13,14,15,16] In contrast, no lineage-specific antigens have been characterized for the acute myeloid leukemias.[18,19] As a result, assignment of leukemic samples to T-lymphoid, myeloid or undifferentiated categories is more difficult, due to the need for more extensive interpretation of the data obtained from both the antigenic and light scatter profiles.

Assigning a lineage to a leukemic cell population is important because different leukemias are treated with different therapies. Accordingly, it is an object of this invention to provide a single, reliable and objective method for classifying leukemias. Once classified, the method further may be used to monitor progression and/or treatment of the disease.

SUMMARY OF THE INVENTION

The present invention comprises a method for classifying leukemias. Initially, a sample of blood or bone marrow cells is obtained from a patient. The cells then are mixed with a plurality of monoclonal antibodies each labelled with a fluorochrome having an emission spectra which is distinguishable from the other. The antibodies may be labelled directly or indirectly by conventional methods. Fluorescence intensities and light scatter parameters for each of the cells then is measured by means of flow cytometry. The relative fluorescence intensities (and/or light scatter parameters) then are scored and the scores are compared with standard scores in order to classify the leukemia.

In one embodiment of the invention, acute leukemias may be classified by combining mononuclear cells which have been separated from a bone marrow sample with a plurality of fluorescently labelled monoclonal antibodies. The cells are separated into a plurality of aliquots. Into each aliquot, two or more antibodies are added. The cells in each aliquot then are analyzed separately by means of flow cytometry and multiple fluorescence and light scatter properties are recorded for each cell in the aliquot. A multi-dimensional plot then is made for fluorescence (and/or light scatter) parameters. The four quadrants (in a two-dimensional plot) for each aliquot then are numbered consecutively such that cells positive for one antibody fall into a first quadrant, cells that are positive for both antibodies fall into a second quadrant, cells that are negative for both antibodies fall into a third quadrant and cells that are positive for the other antibody fall into a fourth quadrant. (As used herein, "quadrant" refers to any region or space in an n-dimensional plot.)

The sequence of the aliquot analysis and antibody pairing is important. Recognizing that acute B-lymphoid leukemias, for example, are more easily distinguished from acute T-lymphoid and myeloid leukemias, the first aliquot is selected so as to include two antibodies that are B cell lineage specific. The remaining aliquots then are sequentially selected to contain other antibody Pairings that will further discriminate between and among B-lymphoid, T-lymphoid, myeloid and undifferentiated leukemias respectively. Accordingly, the same quadrant analysis is done for each antibody pairing; however in recognition of the sequences used, the second aliquot will start with the first quadrant being numbered "5", the third aliquot will start with the first aliquot being numbered "9", etc.

In this embodiment, antibodies that react with B cells include CD10, CD19, CD20, CD22, CD21, CD24, CD26, CD35, CD37, CD39, CD40, CD72, CD75, CD76 and CD79. Antibodies that react with T cells include CD1, CD2, CD3, CD5, CD7 CD4, CD6, CD8 and CD27. Antibodies that react with myeloid cells include CD11b, CD11c, CD13, CD14, CD15, CD16, CD33, CD48, CD63, CD74, CD65, CD66, CD67 and CD68. Antibodies that react with undifferentiated cells include HLA-DR, CD34 and CD38. It should be appreciated that multiple combinations of antibodies selected from the ones mentioned above are possible. While different combinations could result in different scores being representative any given leukemia, the point of the invention is that once a particular set of antibodies is selected which will discriminate between the several types of leukemias a look-up table can be generated from samples of known leukemias. Accordingly, it will be apparent to one skilled in the art that not only can one vary the antibody combinations but also the sequence of analysis and yet still perform the quadrant analysis of the invention.

In a more specific embodiment of the invention for classification of acute leukemias, at least five aliquots of a cell preparation are taken from a patient sample. In sequence, the aliquots contain the following pairs of antibodies: CD10/CD19; CD20/CD5; CD3/CD22; CD7/CD33; and HLA-DR/CD13. In each aliquot, the first antibody of each pair is labelled with one specific fluorochrome (e.g., R-phycoerythrin "PE") and the second antibody of the pair is labelled with another specific fluorochrome that has a fluorescence emission distinguishable from the first (e.g., fluorescein isothiocyanate "FITC"). Separate aliquots also can be provided with fluorescently labelled and unlabelled control antibodies to establish the fluorescent gates above and below which cells which are "positive" for fluorescence can be distinguished from cells which are "negative."

Using this combination of antibodies and fluorochromes, the cells in each aliquot are analyzed by means of flow cytometry. Two-dimensional plots then are made of the data from the cells analyzed (generally this is done for purposes of user visualization, alternatively this step could be accomplished without user interaction by data recording and storage means such as a personal computer), and a score is assigned to each quadrant having greater than a certain percentage of the cell population within that quadrant. Thus, for example, if in the first aliquot, greater than 20% of the cells fell into quadrant "1", the leukemia would be assigned a score of "1". If in the second aliquot, greater than 20% of the cells fell into quadrant "6", the leukemia would also be assigned a score of "6". Each leukemia may have multiple scores. The user manually (or data recording and storage means automatically) then compares the scores assigned (i.e., 1 and 6) with a look-up table which has been developed by applying the above analyses to samples from patients having previously been confirmed to have particular leukemias. Because of the sequence of analysis, a diagnosis may be made from fewer than the total number of scores obtained.

It is to be appreciated that other embodiments of the invention exist. For example, an additional tube containing CD34/CD38 could be added to further disriminate between and classify undifferentiated leukemias. In another example, it is possible to combine three antibodies into a single aliquot. In this embodiment, there will be 8 possible combinations for the cells labelled within the aliquot (i.e.. – – –, + – –, – + –, – – +, + + –, + – +, – + +, + + +). Accordingly, each quadrant will be numbered consecutively "1"–"8", with the first quadrant of the next aliquot commencing with "9". Such three-dimensional analyses is possible using a third fluorochrome (e.g., perdinin chlorophyll complex "PerCp") which has an emission spectra distinguishable from the other two fluorochromes referred to above. Scoring and identification then will proceed as above.

DESCRIPTION OF THE FIGURES

FIG. 1 shows the quadrant numbering scheme used in one embodiment of the invention.

FIG. 3e) when mixed with the reagents from Tube 1 (b), Tube 2 (c), Tube 3 (d), Tube 4 (e), Tube 5 (f), Tube 6 (g) and Tube 7 (h) with the forward and orthogonal light scatter gate for lymphocytes from FIG. 10a applied and the percentage of positive values assigned. (The cells in this figure appear to be normal lymphocytes as discernable by the presence of both B and T cells in the gate.)

FIG. 14 comprises an example of an acute leukemia immunophenotyping worksheet which may be used in one embodiment of the invention.

DETAILED DESCRIPTION

Figure 2A:
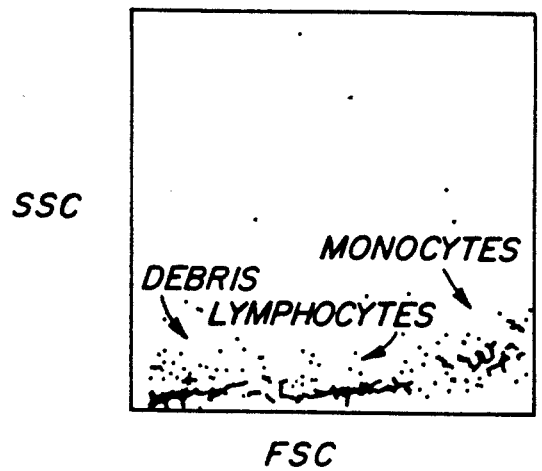
FIG. 2a–FIG. 2c comprises three log dot plots of (a) SSC versus FLC (ungated), (b) FL2 versus FL1 and (c) SSC versus FSC (gated with the lymphocyte gate drawn in (b)).

A heparinized bone marrow aspirate or peripheral blood sample containing greater than 50% blasts is obtained by standard aseptic methods from a study patient already diagnosed with acute leukemia. A fresh peripheral blood sample from a normal donor is obtained by venipuncture[20] to insure proper instrument setup and to serve as a control. Mononuclear cells from bone marrow or peripheral blood are density-gradient separated using Ficoll-Hypaque ™, according to the manufacturer's instructions.

Cell viability, a differential count, and a white blood cell (WBC) count are determined for each sample by standard methods. Samples may be stored or transported at room temperature (20° to 25° C.), but should be separated and stained within 24 hours after collection. The following tubes and reagent combinations can be used and are available from Becton Dickinson Immunocytometry Systems (BDIS):

1 Unstained/Autofluorescence Control
2 Control IgG$_{2a}$ FITC & Control IgG$_1$ PE
3 CD10 (CALLA[21]) FITC & CD19 (Leu-12[22]) PE
4 CD20 (Leu-16[23]) FITC & CD5 (Leu-1[24]) PE
5 CD3 (Leu-4[24]) FITC & CD22 (Leu-14[22]) PE
6 CD7 (Leu-9[24]) FITC & CD33 (Leu-M9[25]) PE
7 Anti-HLA-DR FITC & CD13 (Leu-M7[26]) PE When the monoclonal antibody reagents are added to the separated mononuclear cells, the fluorochrome-labelled antibodies bind specifically to cell-surface antigens. The stained cells fluoresce when they pass through the flow cytometer and are exposed to a 488-nm blue-green laser beam. Use of FITC and PE permits simultaneous two-color analysis, because each fluorochrome emits light at a different wavelength when excited by the laser. The flow cytometer measures the intensity of emitted light at 530 nm for FITC (green) and at 575 for PE (red-orange).

The flow cytometer, for example a FACScan ™ brand flow cytometer, can be optimized for use with normal donor peripheral blood, prior to analyzing leukemic samples in accordance with manufacturer's suggestions. The prepared investigational sample tubes are run on the FACScan, and up to 30,000 ungated events are collected in list mode files. Data files are analyzed using the appropriate computer software and hardware. Dot plot displays of fluorescence and light scatter, along with the corresponding quadrant statistics, then are used in the analysis process.

It is important to differentiate between leukemic cells and normal cells in every study sample, since only leukemic cells are used to assign lineage. Normal lymphocytes will show a characteristic light scatter pattern and antigenic profile. Residual normal lymphocytes may be identified by examining each light scatter gate and displaying fluorescence-1 ("FL1") versus fluorescence-2 ("FL2") dot plots for Tube 5. Residual normal lymphocytes, if present, may be identified by CD3+ and CD22− events for T lymphocytes in quadrant 4, and CD3− and CD22+ events for B lymphocytes in quadrant 1.

For each of the five reagent combinations (Tubes 3 through 7), the percentage of gated events in each quadrant is examined. The quadrants have been numbered from 1 to 20 for the five reagent tube combinations, as shown in FIG. 1. When a sample meets the criteria for percentage positive gated events in a quadrant, the corresponding quadrant numbers (1 through 20) are assigned to the sample. Before a number can be assigned, however, it is important to be sure these positive events represent the antigenic expression on leukemic cells, rather than on residual normal lymphocytes.

The percent positive value is determined for each of the 20 quadrants for each study sample. The percentage of positive events in a quadrant must meet the minimum value for percentage of positive events for the type of antigen being examined. The minimum value for the lymphoid and nonlineage restricted antigens (CD10, CD19, CD20, CD5, CD3, CD22, CD7, or HLA-DR) is greater than 20% positive events in a quadrant. For the myeloid/monocyte antigens (CD33 and CD13) the percentage of positive events in a quadrant must be greater than 30%. These percentages may vary if other combinations of antibodies are used to distinguish these acute leukemias.

When a negative quadrant (i.e., quadrants 3,7,11,15, and 19) contains greater than 30% events, the corresponding quadrant number also should be recorded, as these numbers help identify characteristic patterns of antigens that are not expressed.

The most probable lineage is assigned to the sample by comparing the assigned quadrant numbers for a patient sample with the reference chart shown in Table 2.

The acute leukemia is assigned to either B-lymphoid, T-lymphoid, myeloid or undifferentiated categories. The term "mixed lineage" is not used and some cases that are assigned to B lineage may still express myeloid markers.

analyze the remaining tubes in the sample. See U.S. Pat. No. 4,987,086.

Expression of the CD10 (or common acute lymphoblastic leukemia antigen "CALLA") is reported to be indicative of B-lymphoid lineage leukemias.[3,15,27] Coex-

TABLE II

| Tube | Reagent Pair | Quad. | # | >20% | >30% | Poss. Lin. | Add'l Criteria | Lineage |
|---|---|---|---|---|---|---|---|---|
| 3 | CD10−/CD19+ | Q1 | 1 | x | | B-lymphoid | | * |
| | CD10+/CD19+ | Q2 | 2 | x | | | | B-Lymphoid |
| | CD10−/CD19− | Q3 | 3 | | x | | | ** |
| | CD10+/CD19− | Q4 | 4 | x | | B-lymphoid T-lymphoid or myeloid | | * |
| 4 | CD20−/CD5+ | Q1 | 5 | x | | T-lymphoid or Myeloid | | * |
| | CD20+/CD5+ | Q2 | 6 | x | | | 1 | B-lymphoid |
| | CD20−/CD5− | Q3 | 7 | | x | | | ** |
| | CD20+/CD5− | Q4 | 8 | x | | B-lymphoid | 4 or 1 | B-lymphoid |
| 5 | CD3−/CD22+ | Q1 | 9 | x | | B-lymphoid | 4, 1 or 8 | B-lymphoid |
| | CD3+/CD22+ | Q2 | 10 | | a | | | |
| | CD3−/CD22− | Q3 | 11 | | x | | | ** |
| | CD3+/CD22− | Q4 | 12 | x | | T-lymphoid | 5 | T-lymphoid |
| 6 | CD7−/CD33+ | Q1 | 13 | | x | Myeloid | 3, 7, 11 | Myeloid |
| | CD7+/CD33+ | Q2 | 14 | | x | Myeloid | | * |
| | | | | | | T-lymphoid | 4 or 5 or 12 | T-lymphoid |
| | CD7−/CD33− | Q3 | 15 | | x | | | ** |
| | CD7+/CD33− | Q4 | 16 | x | | T-lymphoid | 4 or 5 or 12 | T-lymphoid |
| 7 | HLA-DR−/CD13+ | Q1 | 17 | | x | Myeloid | 3, 7, 11, 13 (or 14) | Myeloid |
| | HLA-DR+/CD13+ | Q2 | 18 | | x | Myeloid | 3, 7, 11 13 or 14 | Myeloid |
| | HLA-DR−/CD13− | Q3 | 19 | | x | | | ** |
| | HLA-DR+/CD13− | Q4 | 20 | | x | Myeloid | 3, 7, 11, 13 or 14 | Myeloid |
| | | | | | | Undiff. | 3, 7, 11, 15 | Undiff. |
| | | | | | | B-lymphoid | 1 or 8 or 9 | B-lymphoid |
| | | | | | | T-lymphoid | 3, 5, 12, 16 | T-lymphoid |

*Additional information is needed to assign lineage.
**Q3 normally contains unstained cells.
ªUnlikely.

The unstained control is prepared along with the stained samples. This tube is used to assess background fluorescence, and to establish the appropriate light scatter gate(s) around the predominant cell cluster(s). A separate gate is drawn around each distinct population id a display of forward light scatter ("FLC") versus side scatter ("SSC"). The settings for the light scatter gate are maintained during analysis of subsequent tubes for each patient sample. All tubes should be evaluated for each gate that is drawn. (This may be done visually by the operator or may be done by means of software associated with the data recording and storage means.)

The fluorescence control tube containing the control IgG$_{2a}$ FITC and the control IgG$_1$ PE is used to establish the FL1 and FL2 markers around the negative population. Fluorescence marker settings are then used to pression of CD10 and CD19 antigens on greater than 20% of the gated cells has been found to indicate acute leukemias of the B-lymphoid lineage.[3] The presence of the CD19 antigen on greater than 20% of the gated cells suggests a B-lymphoid lineage leukemia, but additional confirmation is required. The presence of the CD10 antigen on greater than 20% of the gated cells can indicate B-lymphoid, T-lymphoid or myeloid lineage leukemias, and therefore, additional information is needed. Confirmation is obtained using the CD20/CD5, CD3/CD22 HLA-DR/CD13 and CD33/CD7 combinations. If coexpression of the CD10 antigen and CD19 antigens is less than 20%, B-lymphoid lineage leukemia is unlikely.

Coexpression of CD20 and CD5 has been considered suggestive of a B-lymphoid lineage leukemia.[3,28,29] The presence of the CD20 antigen on greater than 20% of the gated cells, if either CD10 or CD19 also is expressed, is thought to aid in confirming a B-lymphoid lineage acute leukemia. Presence of the CD20 antigen on greater than 20% of the gated cells, in the absence of CD5, CD10 or CD19 antigens, suggest a B-lymphoid lineage leukemia, but requires additional confirmation. Confirmation is obtained using the CD3/CD22 and HLA-DR/CD13 combinations. The presence of the CD5 antigen on greater than 20% of the gated cells, in the absence of CD10, CD19 and CD20 antigens, may indicate either a T-lymphoid lineage or myeloid lineage leukemia, but additional conformation is required using the results obtained from analysis of subsequent tubes.

The presence of the CD3 antigen on greater than 20% of the gated cells indicates a T-lymphoid lineage leukemia, when the CD5 antigen also is expressed on greater than 20% of the gated cells. Normal B and T lymphocytes must first be excluded. The presence of CD22 on greater than 20% of the gated cells, when either CD10, CD19 or CD20 antigen is coexpressed, confirms a B-lymphoid lineage leukemia.[30,31]

The CD3/CD22 reagent combination may be used to determine the relative number of normal T lymphocytes in the light scatter gate for patients with B-lymphoid or myeloid lineage leukemias. This combination also may be used to determine the relative number of normal B lymphocytes for patients with acute T-lymphoid or myeloid lineage leukemias. When present, these residual T or B lymphocytes provide an additional internal control to determine if the flow cytometer has been set up correctly.

The presence of the CD7 antigen in the absence of CD10, CD19, CD20 and CD22 antigens has been reported to indicate T-lymphoid or myeloid lineage leukemias. Coexpression of CD5 and CD7 on greater than 20% of the gated cells is suggestive of T-lymphoid lineage leukemia, but confirmation is required since these markers also may be expressed in acute myeloid lineage leukemias.[13,14,16] T-lymphoid lineage is assigned when the CD3, CD5 and CD7 antigens are coexpressed.

The myeloid-associated antigens, CD33 and CD13, are considerably less specific for the myeloid lineage as compared with the specificity of the CD19, CD20 and CD22 antigens for the B-lymphoid lineage. The CD33 and CD13 antigens can be expressed in lymphoid as well as myeloid leukemias.[13,16,30,32] Furthermore, a large proportion of normal bone marrow cells express the CD33 antigen, whereas the B-lymphoid antigens, CD10 and CD19, are found infrequently on normal bone marrow cells.[12] As a consequence, the presence of myeloid antigens is a less sensitive indicator of leukemic disease than the presence of B-lymphoid antigens. The presence of CD33 antigen on greater than 30% of the gated cells, in the absence of CD3, CD5, CD7, CD10, CD19, CD20 and CD22 antigens, assigns the sample to myeloid lineage. The coexpression of CD33 and CD7 on greater than 30% of the gated cells, in the presence of either CD13 or HLA-DR antigens and the absence of other T-lymphoid antigens, is indicative of myeloid lineage.

Consideration of antigen density is especially important for correct lineage assignment when antigens are aberrantly expressed. Populations that appear at the higher channel numbers in one of the positive quadrants stain brightly and have a high antigen density. Populations that appear in a positive quadrant, but which are located closer to the FL1 and FL2 fluorescence markers, stain dimly and have a lower antigen density.

Bright fluorescence staining of CD7 and dim fluorescence staining of CD33 suggest T-lymphoid lineage, whereas dim CD7 staining and bright CD33 staining suggest myeloid lineage. Coexpression of the CD7 and CD33 antigens can also be found in B-lymphoid lineage, but in most cases the staining is dim.[15,30,31]

Presence of the HLA-DR antigen, a major histocompatibility complex (MHC) Class II antigen, has been described in acute myeloid, lymphoid, and undifferentiated leukemias.[3,4,5,33] Coexpression of the HLA-DR and CD13 antigens suggests myeloid lineage. Nevertheless, B- and T-lymphoid lineages must first be excluded using the information obtained from the antibody combinations described above.

Expression of the CD13 antigen indicates myeloid lineage when B- and T-lymphoid leukemias are excluded using the above criteria. When CD13 and CD33 are coexpressed on the gated cells, lymphoid lineage leukemia must first be excluded, using the above criteria, before assigning the leukemia to the myeloid lineage. Expression of the HLA-DR antigen without expression of B-lymphoid, T-lymphoid, or myeloid lineage antigens indicates acute undifferentiated leukemia.

EXAMPLE 1

Heparinized bone marrow aspirates were collected aseptically. Alternatively, peripheral blood samples, containing greater than 50% leukemic blast cells, were collected aseptically by venipuncture into a sterile K3 EDTA VACUTAINER TM brand blood collection tube. The percentage of blasts present was determined by evaluation of the Wright-Giemsa stain smear and by performing a standard differential count.

A minimum of $7 \times 10^6$ cells at a concentration of $2 \times 10^7$ nucleated cells/mL are required after density-gradient separation.

Mononuclear cell suspensions were obtained by density-gradient separation. A white blood cell (WBC) count and a standard differential count were performed on separated cells. Cell viability was determined using ethidium bromide and acridine orange staining.

Separated cell suspensions of bone marrow aspirates and/or peripheral blood then were mixed with FITC labelled reagents, washed, and then stained with PE labelled reagents. The samples then were applied to a flow cytometer.

Figure 2B:
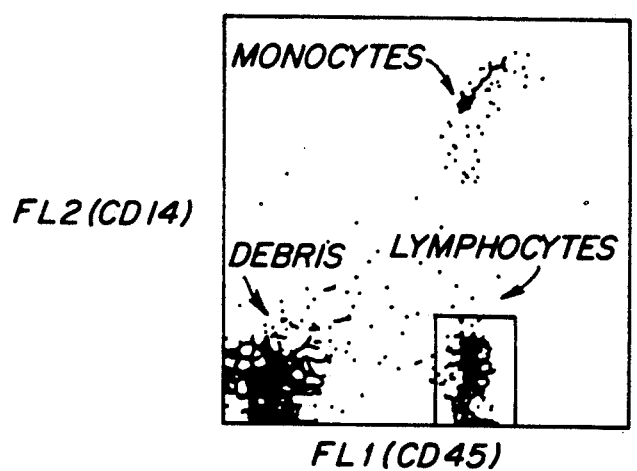
Figure 2C:
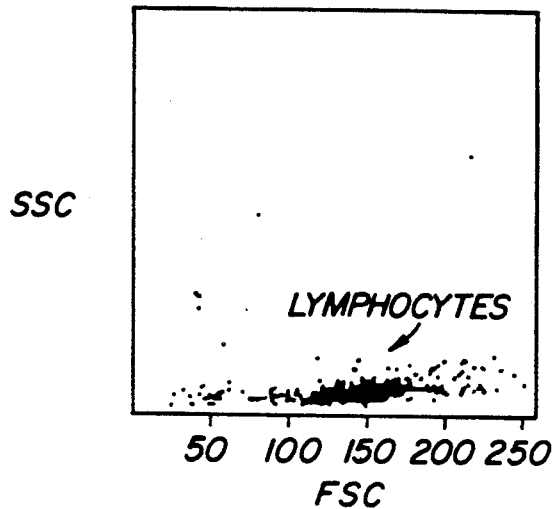

Human peripheral blood samples from a normal donor were run prior to running investigational leukemic samples in order to optimize the instrument/reagent test system since high autofluorescence staining and unusual light scatter patterns are often present in samples from acute leukemia patients. Moreover, the various light scatter patterns obtained with acute leukemias may be of interest. Therefore, optimal instrument setup may permit differentiation between types of acute leukemias. FIG. 2 displays a typical series of dot plots for normal peripheral blood cells when mixed with anti-CD45 FITC and anti-CD14 PE reagents (BDIS) before optimization. (This combination of antibodies is particularly useful in discriminating between normal lymphocytes, normal monocytes and debris and which will give a good indication of whether the instrument is properly set up and aligned in accordance with the manufacturer's specifications and procedures.)

Live data was acquired on a FACScan brand flow cytometer using LYSYS II software (BDIS). Up to 30,000 events per sample in list mode. The patient data was saved and stored to allow subsequent analysis of data files. The LYSYS II software allows flexible gates to be drawn around distinct populations of leukemic and/or normal cells.

Figure 3A:
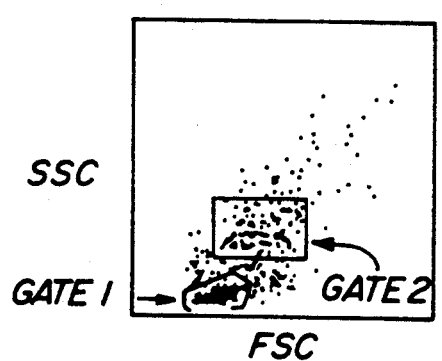
FIG. 3a–FIG. 3f comprises a series of log dot plots of SSC versus FSC for (a) normal peripheral blood and bone marrow cells from patients with (b) B-lymphoid, (c) T-lymphoid, (d) Myeloid, (e) Myeloid and (f) Myeloid acute leukemias with light scatter gates drawn around each distinct population of cells in (a), (e) and (f).
Figure 3B:
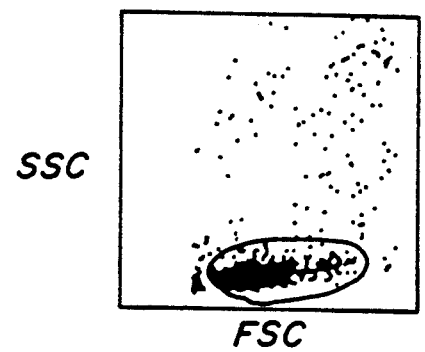
Figure 3C:
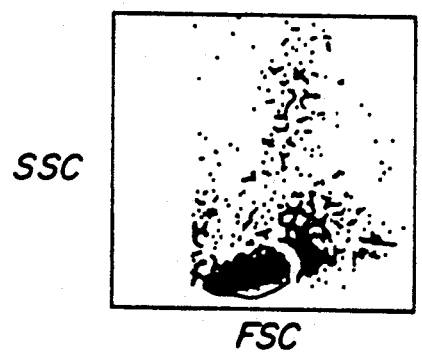
Figure 3D:
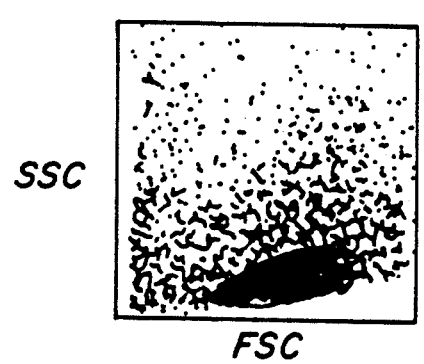
Figure 3E:
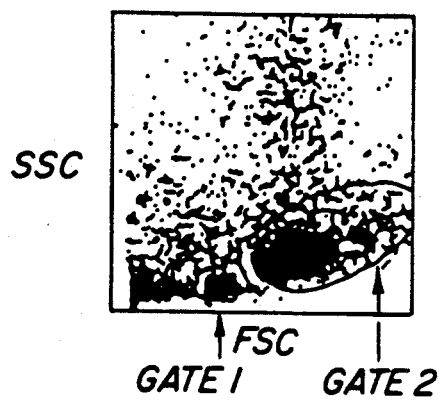
Figure 3F:
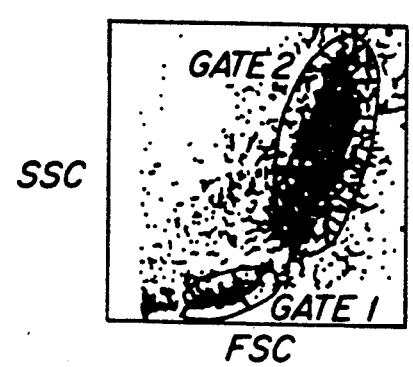
Figure 4A:
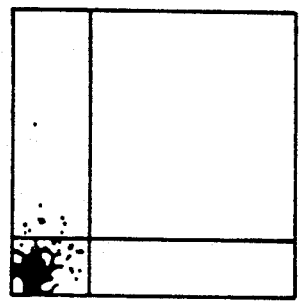
FIG. 4a–FIG. 4i comprises a series of log dot plots of log FL2 versus log FL1 for the cells from FIG. 3 which have been labelled with $IgG_1$ PE and $IgG_{2a}$ FITC wherein (a) comprises the cells from FIG. 3a (gate 1), (b) comprises the cells from FIG. 3a (gate 2), (c) comprises the cells from FIG. 3b, (d) comprises the cells from FIG. 3c, (e) comprises the cells from FIG. 3d, (f) comprises the cells from FIG. 3e (gate 1), (g) comprises the cells from FIG. 3e (gate 2), (h) comprises the cells from FIG. 3f (gate 1) and (i) comprises the cells from FIG. 3f (gate 2).
Figure 4B:
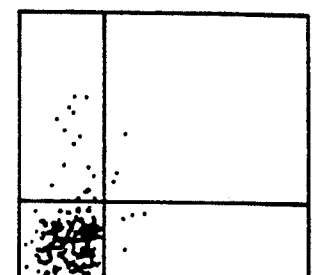
Figure 4C:
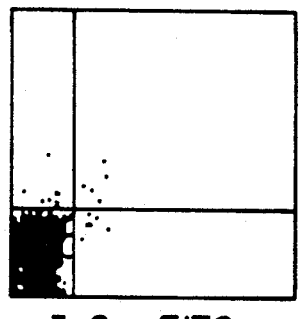
Figure 4D:
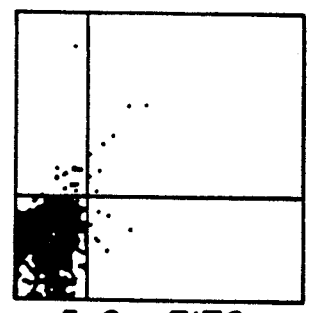
Figure 4E:
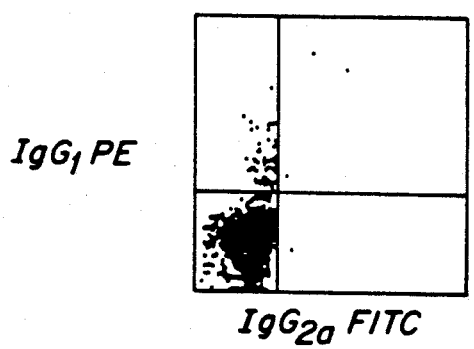
Figure 4F:
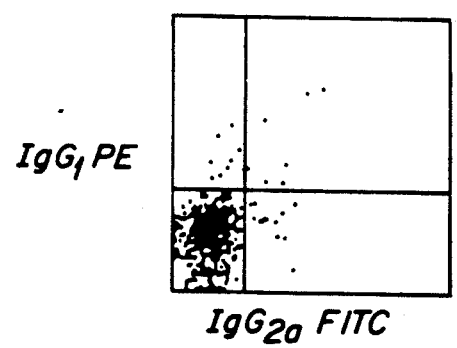
Figure 4G:
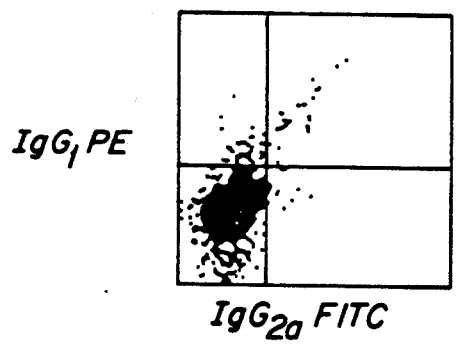
Figure 4H:
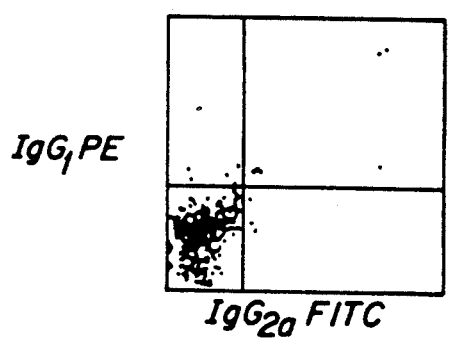
Figure 4I:
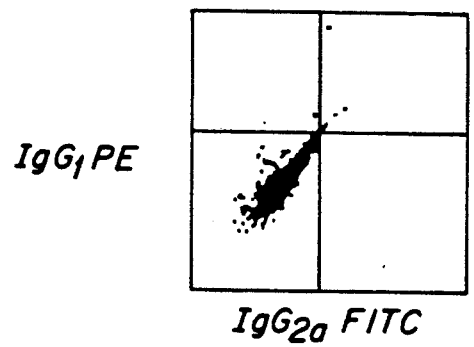

Using data obtained with the unstained control (tube 1), a dot plot of FSC versus SSC was displayed. A light scatter gate was drawn around the predominant cell cluster. If more than one population was apparent, a separate gate was drawn around each population. Representative FSC versus SSC plots, illustrated in FIG. 3, included mononuclear cell preparations of normal peripheral blood and bone marrow aspirates from patients with acute leukemia. Examples include a normal donor (FIG. 3a), a patient diagnosed with acute B-lymphoid leukemia (FIG. 3b), a patient diagnosed with acute T-lymphoid leukemia (FIG. 3c), and three patients diagnosed with acute myeloid leukemia (FIGS. 3d, 3e, 3f). More than one population was apparent in FIGS. 3a, 3e, and 3f; therefore, two light scatter gates were drawn for each of these samples.

A dot plot of FL1 versus FL2 next was displayed for the fluorescence control, tube 2. The fluorescence intensity markers were set tightly around the negative population, which is the cluster of events that is low in both green and red-orange fluorescence, as illustrated in FIG. 4. When more than one population was present and, therefore, more than one light scatter gate was set, fluorescence markers were set independently for each gate. The dot plots in FIG. 4 correspond to the samples and light scatter gates illustrated in FIG. 3. The light scatter gate(s) and fluorescence marker(s) were used for the subsequent analysis and collection of quadrant statistics for tubes 3 through 7.

It is important to differentiate between leukemic cells and normal lymphocytes in the sample. This is done by displaying FL1 versus FL2 dot plots for tube 5 for each light scatter gate and looking for the presence of normal lymphocytes. If they are present, residual normal lymphocytes may be identified by CD3+/CD22− events for T lymphocytes in quadrant 4, and CD3−/CD22+ events for B lymphocytes in quadrant 1. These normal lymphocytes should not be included when assigning lineage.

For each study patient sample, the percentage of positive events in each quadrant was examined. A sample was assigned a quadrant number when the percentage of positive staining events is greater than 20% for lymphoid antigens, or greater than 30% for myeloid antigens. A worksheet such as the one shown in FIG. 14 may be used to record the results.

The full sequence of analysis for the examples illustrated in FIGS. 3 and 4 is shown in FIGS. 5 through 13. The percentages of positive staining cells in each quadrant are shown on the dot plots for reference. The percentage of positive events for each quadrant from the software printout was transferred to the worksheet (FIG. 14), and then assigned quadrant numbers based on the criteria provided above. Lineage assignment based on the quadrant numbers assigned then was determined, using Table 2. Positive events that were due to residual normal lymphocytes in the sample were not be used to assign lineage.

Figure 5A:
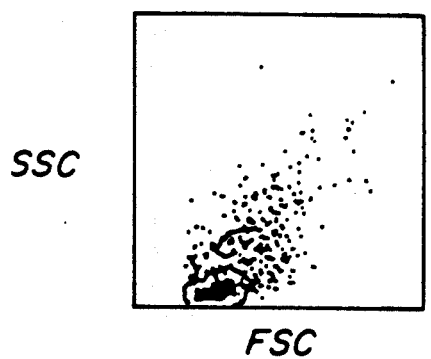
FIG. 5a–FIG. 5h comprises a series of log dot plots of (a) SSC versus FSC and (b–h) FL2 versus FL1 for normal peripheral blood cells when mixed with the reagents from Tube 1 (b), Tube 2 (c), Tube 3 (d), Tube 4 (e), Tube 5 (f), Tube 6 (g) and Tube 7 (h) with the lymphocyte gate (i.e.. 1) from FIG. 3a applied.
Figure 5B:
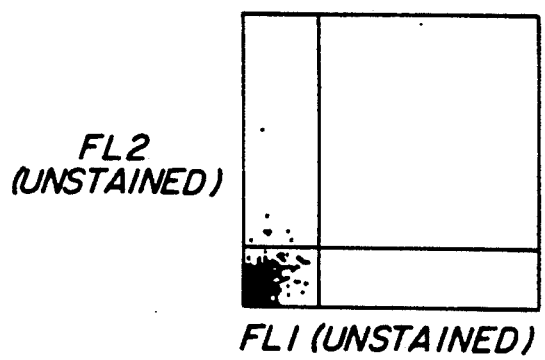
Figure 5C:
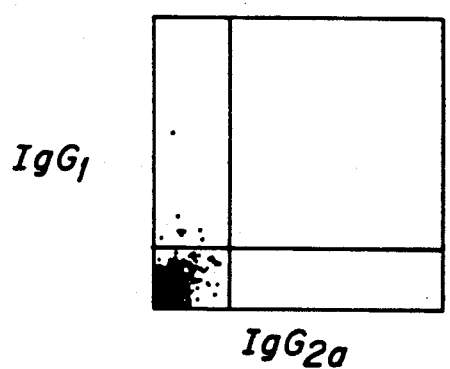
Figure 5D:
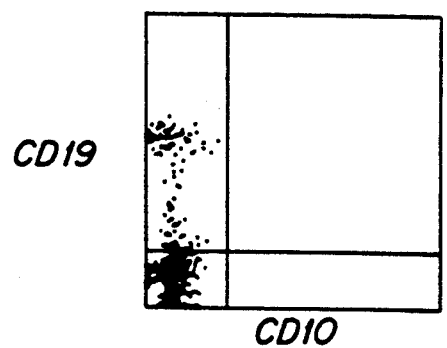
Figure 5E:
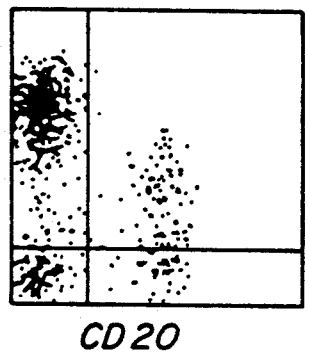
Figure 5F:
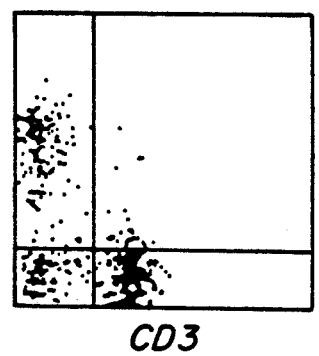
Figure 5G:
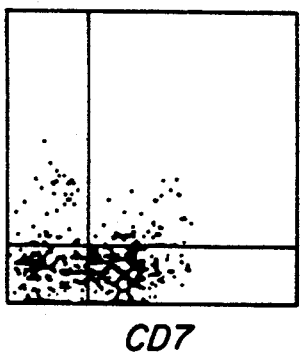
Figure 5H:
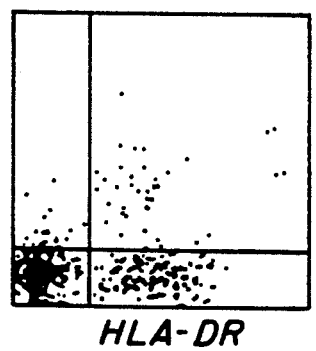
Figure 6A:
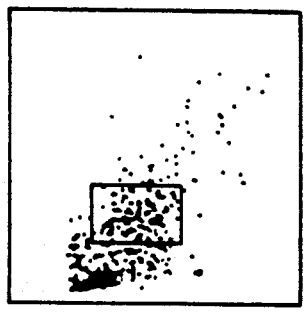
FIG. 6a–FIG. 6h comprises the series of log dot plots from FIG. 5 with the monocyte gate (i.e.. 2) from FIG. 3a applied.
Figure 6B:
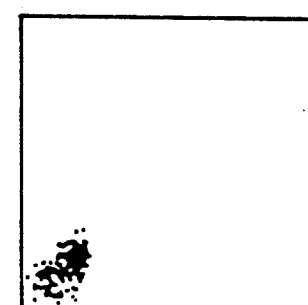
Figure 6C:
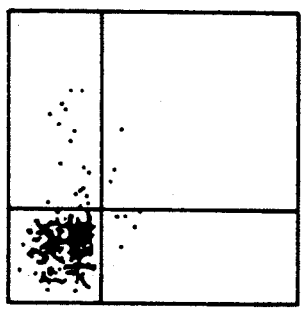
Figure 6D:
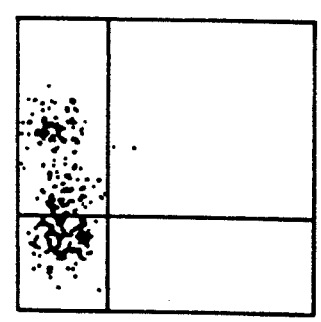
Figure 6E:
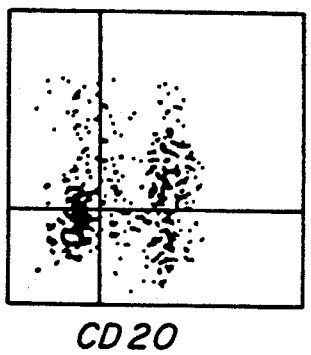
Figure 6F:
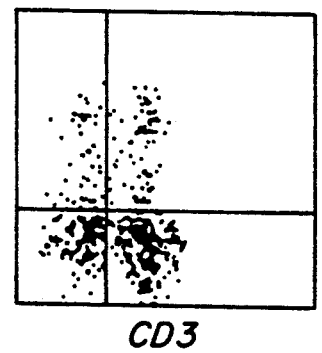
Figure 6G:
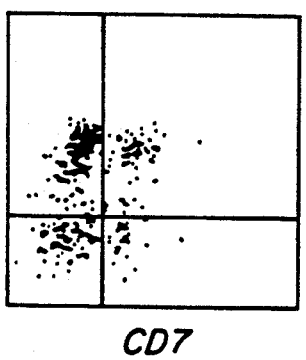
Figure 6H:
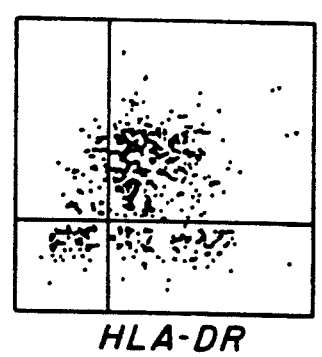

FIGS. 5 and 6 illustrate the analysis of the normal peripheral blood sample using the two separate light scatter gates, shown in FIGS. 5a and 6a. FIG. 5 clearly illustrates a normal distribution of B lymphocytes (CD19+, CD20+, and CD22+) and T lymphocytes (CD5+, CD7+, and CD3+), NK lymphocytes (CD7+) CD5+ B lymphocytes and basophils (CD13+ and CD33+) within this lymphocyte light scatter gate.

In FIG. 6, the plots are displayed for the same normal donor, but now with a monocyte light scatter gate (FIG. 6a). FIGS. 6g and 6h illustrate that the majority of the cells in this gate are monocytes (CD13+, CD33+, and HLA-DR+). (Note the increase in nonspecific fluorescence of the isotype controls (FIG. 6c) as compared with the unstained control (FIG. 6b), due to binding with monocyte Fc receptors.)

FIG. 7 demonstrates the analysis of an acute B-lymphoid leukemia. The majority of the cells coexpress the CD10, CD19, CD22 and HLA-DR antigens Approximately half of the leukemic cells coexpress the CD13 antigen aberrantly. The presence of normal residual T lymphocytes within the light scatter gate is shown in FIGS. 7e, 7f and 7g.

Plots of an acute T-lymphoid leukemia appear in FIG. 8. The majority of the cells coexpress the CD3, CD5, CD7, and HLA-DR antigens. The presence of normal residual B lymphocytes within the light scatter gate is shown in FIGS. 8d, 8e and 8f.

The plots in FIG. 9 illustrate an acute myeloid leukemia. The majority of the cells coexpress the CD13, CD33, and HLA-DR antigens. (Note the presence of normal B and T lymphocytes within the light scatter gate (FIGS. 9d through 9h)).

Figure 10A:
FIG. 10a–FIG. 10h comprises a series of log dot plots of (a) SSC versus FSC and (b–h) FL2 versus FL1 for bone marrow cells from the patient with acute myeloid leukemia (i.e..
Figure 10B:
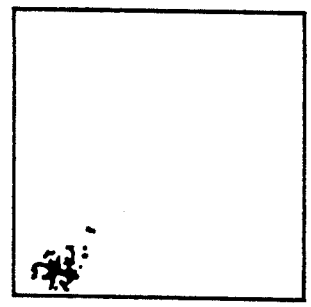
Figure 10C:
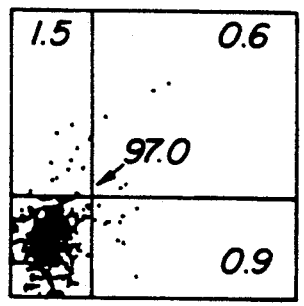
Figure 10D:
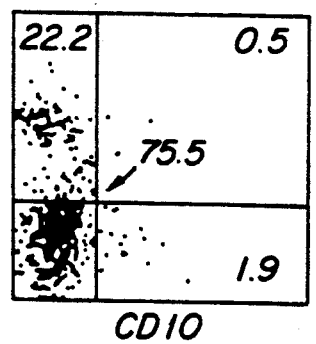
Figure 10E:
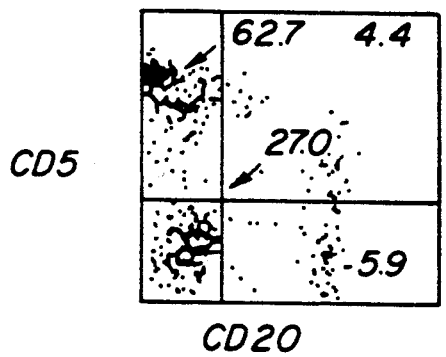
Figure 10F:
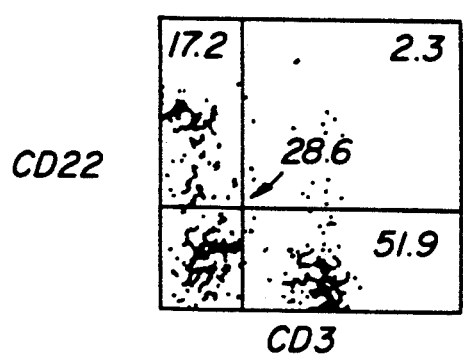
Figure 10G:
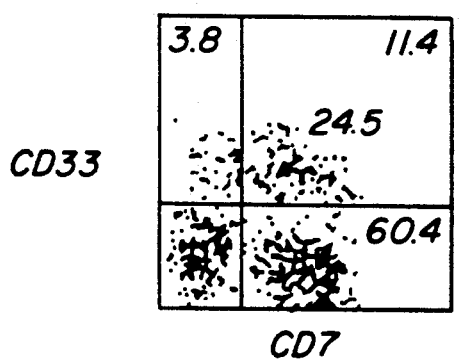
Figure 10H:
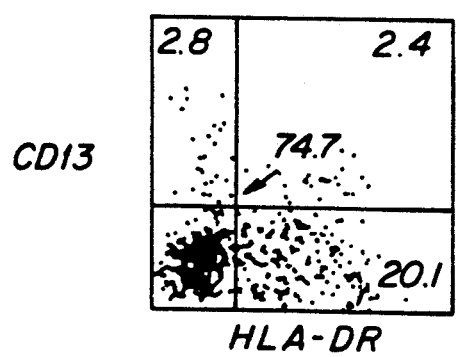
Figure 11A:
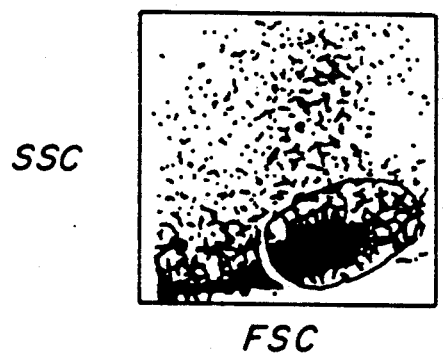
FIG. 11a–FIG. 11h comprises a series of log dot plots of (a) SSC versus FSC and (b–h) FL2 versus FL1 for bone marrow cells from the patient with acute myeloid leukemia (i.e., FIG. 3e) when mixed with the reagents from Tube 1 (b), Tube 2 (c), Tube 3 (d), Tube 4 (e), Tube 5 (f), Tube 6 (g) and Tube 7 (h) with the forward and orthogonal light scatter gate for lymphocytes from FIG. 11a applied, the percentage of positive values and quadrant numbers assigned(i.e., 3, 7, 11, 14, 18, 20).
Figure 11B:
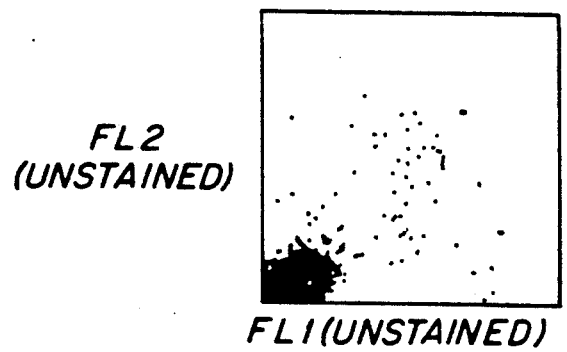
Figure 11C:
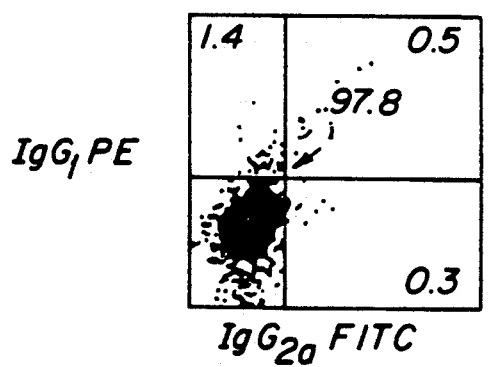

FIGS. 10 and 11 also show the analysis of an acute myeloid leukemia using two separate light scatter gates, as shown in FIGS. 10a and 11a. The majority of the cells within the light scatter gate of FIG. 10a show typical features of normal B and T lymphocytes and thus are not considered part of the leukemic cell population (FIGS. 10d through 10h).

Figure 11D:
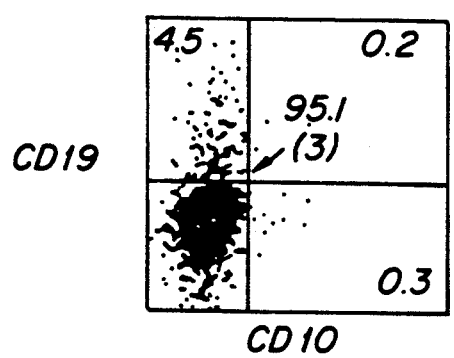
Figure 11E:
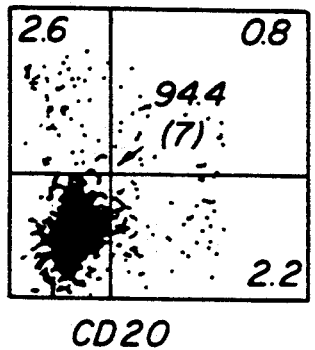
Figure 11F:
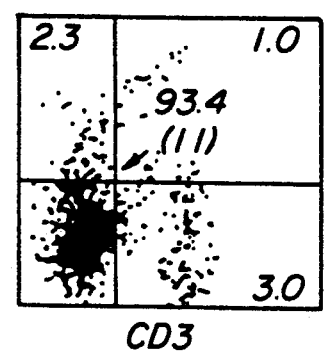

In FIG. 11, only a few of the gated events express features of normal B and T lymphocytes (FIGS. 11e and 11f). The majority of the cells coexpress the CD13, CD33, and HLA-DR antigens and aberrantly express the CD7 antigen. (Note that in this sample, the leukemic cell population consists of multiple populations with distinct features (FIGS. 11g and 11h)).

Figure 12A:
FIG. 12a–FIG. 12h comprises a series of log dot plots of (a) SSC versus FSC and (b–h) FL2 versus FL1 for bone marrow cells from the patient with acute myeloid leukemia (i.e., FIG. 3f) when mixed with the reagents from Tube 1 (b), Tube 2 (c), Tube 3 (d), Tube 4 (e), Tube 5 (f), Tube 6 (g) and Tube 7 (h) with the forward and orthogonal light scatter gate for lymphocytes from FIG. 12a applied and the percentage of positive values assigned. (The cells in this figure appear to be normal lymphocytes as discernable by the presence of both B and T cells in the gate.)
Figure 12B:
Figure 12C:
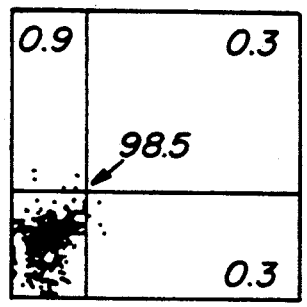
Figure 12D:
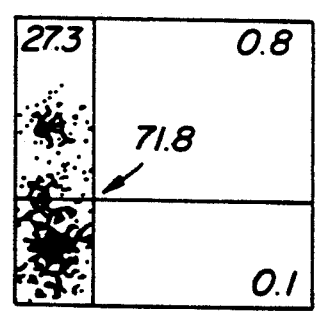
Figure 12E:
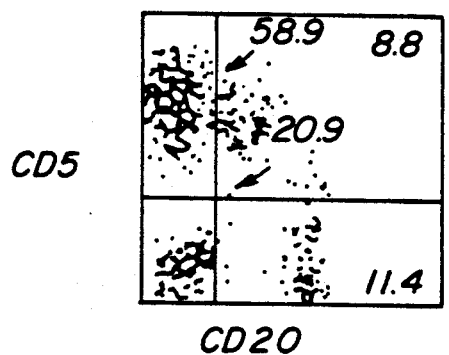
Figure 12F:
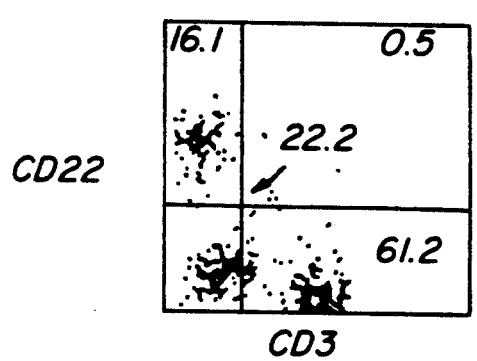
Figure 12G:
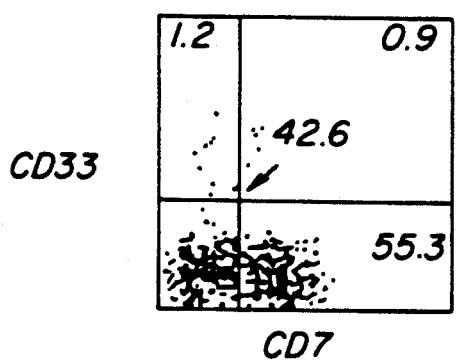
Figure 12H:
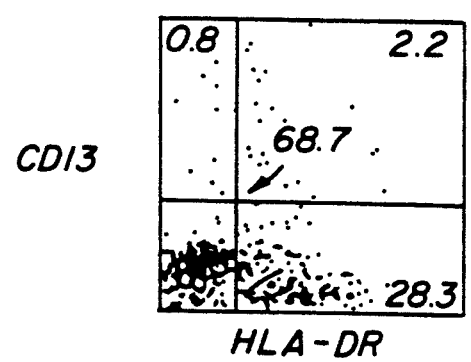
Figure 13A:
FIG. 13a–FIG. 13h comprises a series of log dot plots of (a) SSC versus FSC and (b–h) FL2 versus FL1 for bone marrow cells from the patient with acute myeloid leukemia (i.e., FIG. 3f) when mixed with the reagents from Tube 1 (b), Tube 2 (c), Tube 3 (d), Tube 4 (e), Tube 5 (f), Tube 6 (g) and Tube 7 (h) with the forward and orthogonal light scatter gate for lymphocytes from FIG. 13a applied, the percentage of positive values and quadrant numbers assigned (i.e.. 3, 7, 11, 13, 19).
Figure 13B:
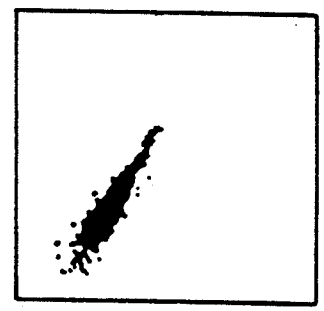
Figure 13C:
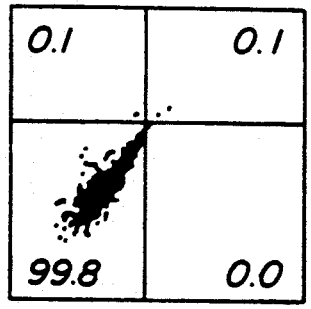

FIGS. 12 and 13 illustrate the analysis of another acute myeloid leukemia by using two separate light scatter gates (FIGS. 12a and 13a). The majority of the cells within the light scatter gate (FIG. 12a) show the typical features of normal B and T lymphocytes and therefore should not be considered as part of the leukemic cell population (FIGS. 12d through 12g). The cells in the light scatter gate of FIG. 13a are in the location of normal and abnormal promyelocytes.[8,17] These cells have high autofluorescence (FIGS. 13b and 13c). The majority of the cells within the light scatter gate of FIG. 13a express the CD33 antigen. The CD13 antigen is expressed by only a small portion of the gated events.

Using the logical decision scheme presented in Table 2, data were analyzed for samples illustrated in FIGS. 7 through 13.

Figure 7A:
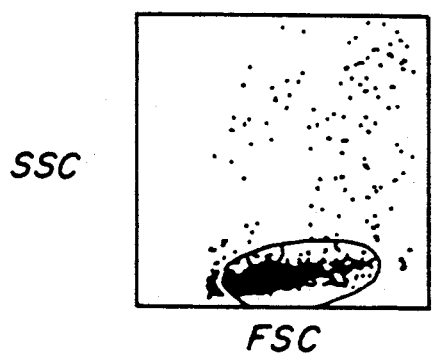
FIG. 7a–FIG. 7h comprises a series of log dot plots of (a) SSC versus FSC and (b–h) FL2 versus FL1 for bone marrow cells from the patient with acute B-lymphoid leukemia (i.e., FIG. 3b) when mixed with the reagents from Tube 1 (b), Tube 2 (c), Tube 3 (d), Tube 4 (e), Tube 5 (f), Tube 6 (g) and Tube 7 (h) with the lymphocyte gate from FIG. 7a applied, the percentage of positive values and quadrant numbers assigned (i.e., 2, 7, 9, 15, 18, 20).
Figure 7B:
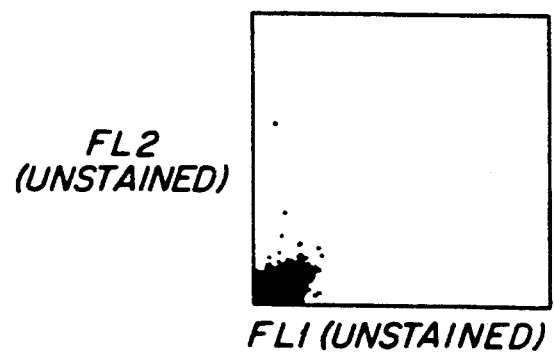
Figure 7C:
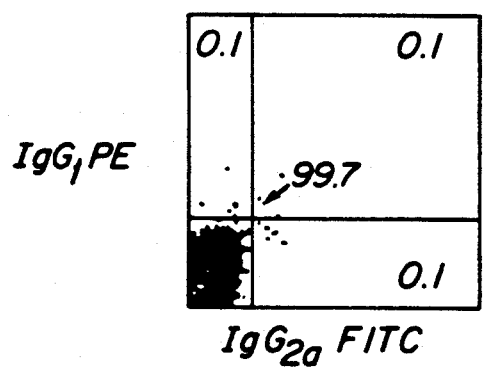
Figure 7D:
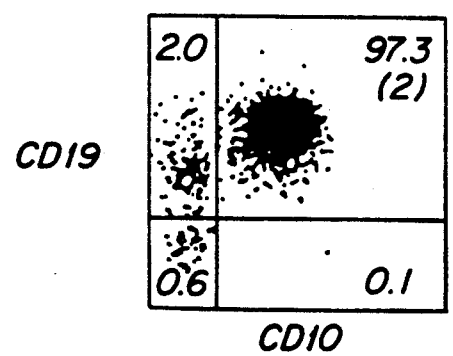
Figure 7E:
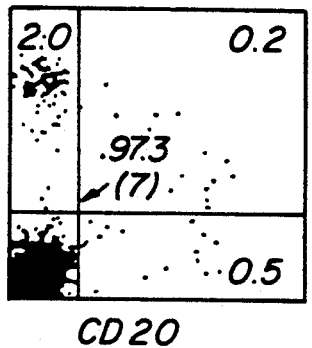
Figure 7F:
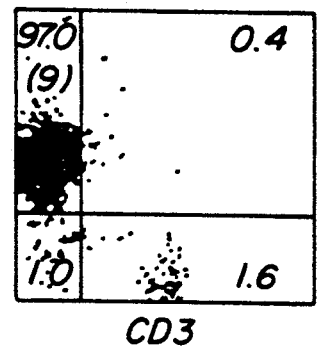
Figure 7G:
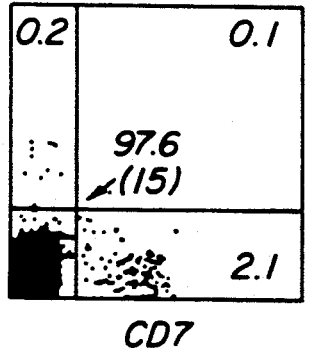
Figure 7H:
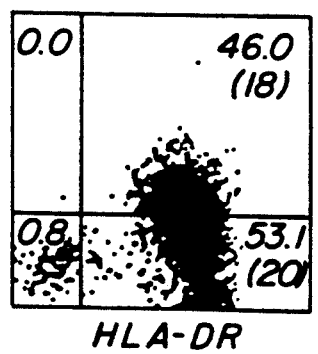

The following numbers were assigned to the sample illustrated in FIG. 7 by examination of the quadrant statistics: 2 to FIG. 7d (greater than 20% coexpress CD19 and CD10); 7 to FIG. 7e (greater than 30% did not express CD5 and CD20); 9 to FIG. 7f (greater than 20% expressed CD22 and lacked CD3); 15 to FIG. 7g (greater than 30% did not express CD7 and CD33); 18 and 20 to FIG. 7h (greater than 30% coexpress CD13 and HLA-DR and greater than 30% lacked CD13 and expressed HLA-DR). The assignment of the lineage is already obtained with the first number (2) and assigns a B lineage to the acute leukemia. Numbers 7, 9, 15, 18, and 20 are additional information on the antigenic profile of this sample.

Figure 8A:
FIG. 8a–FIG. 8h comprises a series of log dot plots of (a) SSC versus FSC and (b–h) FL2 versus FL1 for bone marrow cells from the patient with acute T-lymphoid leukemia (i.e., FIG. 3c) when mixed with the reagents from Tube 1 (b), Tube 2 (c), Tube 3 (d), Tube 4 (e), Tube 5 (f), Tube 6 (g) and Tube 7 (h) with the lymphocyte gate from FIG. 8a applied, the percentage of positive values and quadrant numbers assigned (i.e., 3, 5, 12, 16, 20).
Figure 8B:
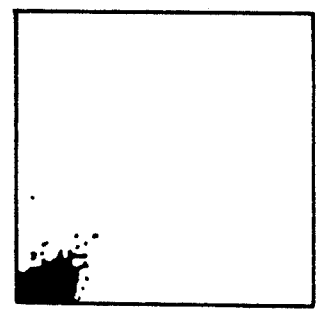
Figure 8C:
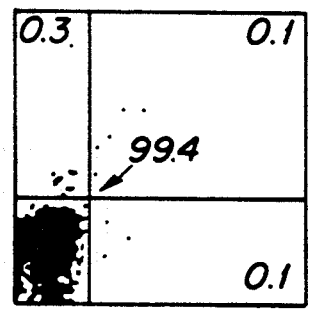
Figure 8D:
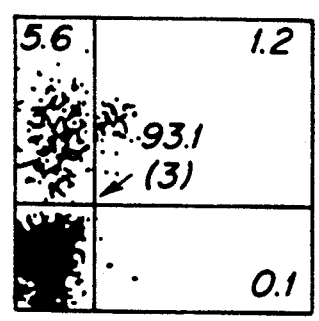
Figure 8E:
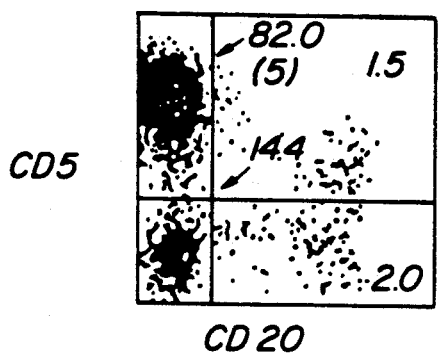
Figure 8F:
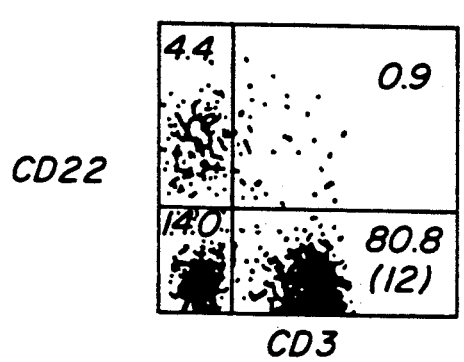
Figure 8G:
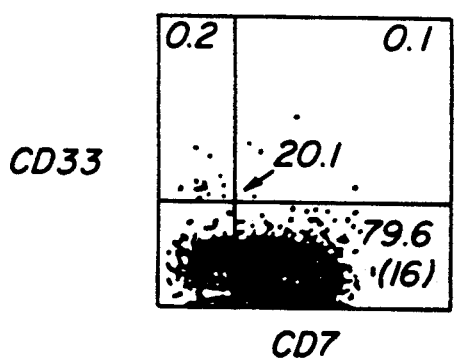
Figure 8H:
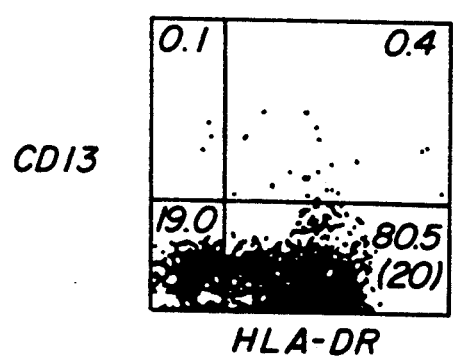

The following numbers are assigned to the sample illustrated in FIG. 8 by examination of the quadrant statistics: 3 to FIG. 8d (greater than 30% lacked CD19 and CD10); 5 to FIG. 8e (greater than 20% did express CD5 and did not express CD20); 12 to FIG. 8f (greater than 20% expressed CD3 and lacked CD22); 16 to FIG. 8g (greater than 20% expressed CD7 and did not express CD33); 20 to FIG. 8h (30% lacked CD13 and expressed HLA-DR). The assignment of the lineage is obtained after the fourth number (i.e., 3, 5, 12, 16, 20) and assigns T lineage to the acute leukemia. The number 20 is additional information on the antigenic profile of this sample.

Figure 9A:
FIG. 9a–FIG. 9h comprises a series of log dot plots of (a) SSC versus FSC and (b–h) FL2 versus FL1 for bone marrow cells from the patient with acute myeloid leukemia (i.e., FIG. 3d) when mixed with the reagents from Tube 1 (b), Tube 2 (c), Tube 3 (d), Tube 4 (e), Tube 5 (f), Tube 6 (g) and Tube 7 (h) with the lymphocyte gate from FIG. 9a applied, the percentage of positive values and quadrant numbers assigned (i.e., 3, 7, 11, 13, 18).
Figure 9B:
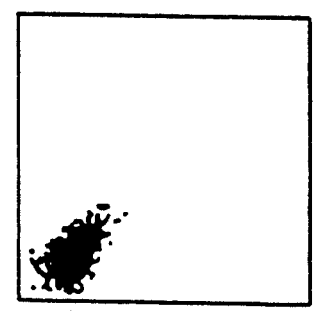
Figure 9C:
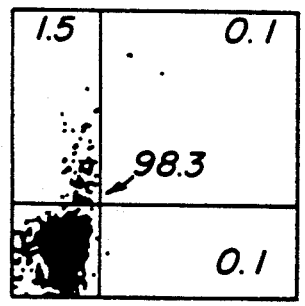
Figure 9D:
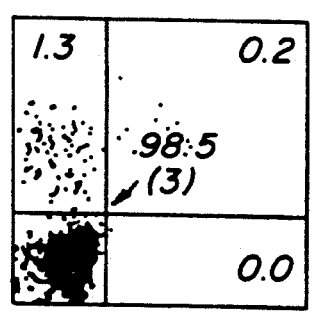
Figure 9E:
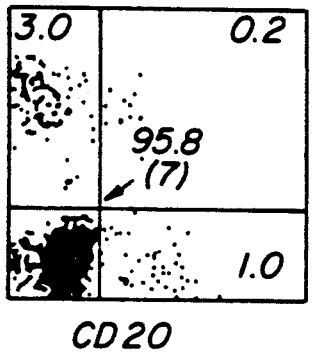
Figure 9F:
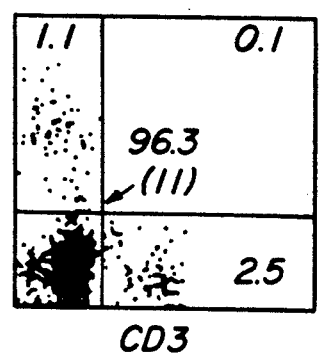
Figure 9G:
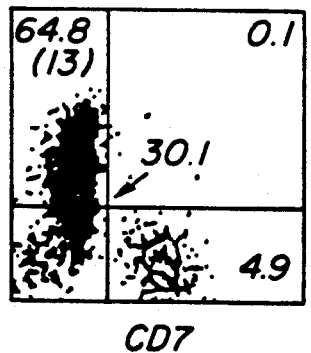
Figure 9H:
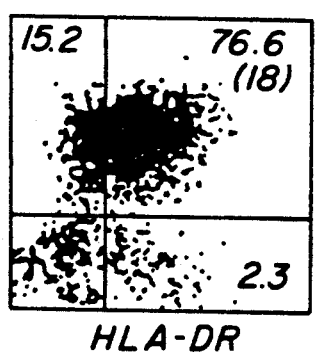

The following numbers are assigned to the sample illustrated in FIG. 9 by examination of the quadrant statistics: 3 to FIG. 9d (greater than 30% did not express CD19 and CD10); 7 to FIG. 9e (greater than 30% did not express CD5 and CD20); 11 to FIG. 9f (greater than 30% lacked CD3 and CD22); 13 to FIG. 9g (greater than 30% express CD33 and did not express CD7); 18 FIG. 9h (greater than 30% coexpress CD13 and HLA-DR ). The assignment of the lineage is obtained after the fourth number (i.e.. 3, 7, 11, 13, 18) and assigns myeloid lineage to the acute leukemia. The number 18 gives additional information on the antigenic profile of this sample.

Figure 11G:
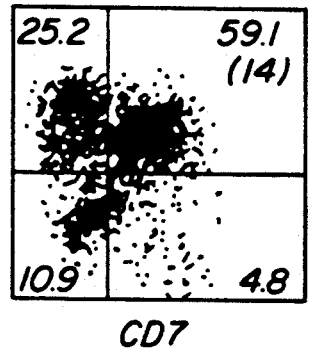
Figure 11H:
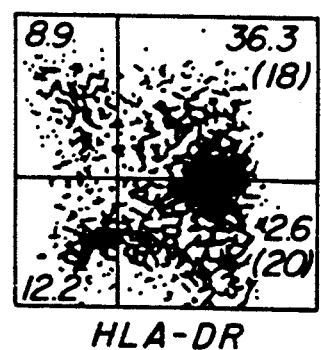

The following numbers are assigned to the sample illustrated in FIG. 11 by examination of the quadrant statistics: 3 to FIG. 11d (greater than 30% did not express CD19 and CD10); 7 to FIG. 11e (greater than 30% did not express CD22); 14 to FIG. 11g (greater than 30% coexpress CD33 and CD7); 18 and 20 to FIG. 11h (greater than 30% coexpress CD13 and HLA-DR and greater than 30% express HLA-DR and lack CD13). The assignment of the lineage is obtained after the fourth number (i.e., 3, 7, 11, 14, 18, 20) and assigns myeloid lineage to the acute leukemia. The numbers 18 and 20 give additional information on the antigenic profile of this sample.

Figure 13D:
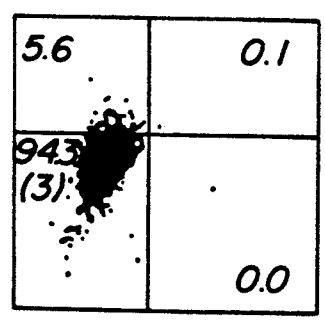
Figure 13E:
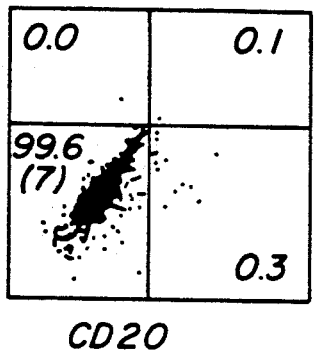
Figure 13F:
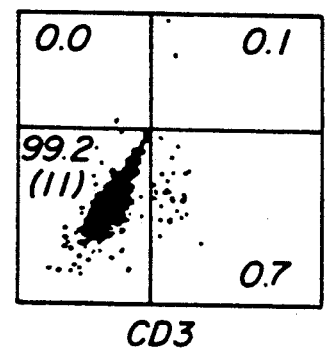
Figure 13G:
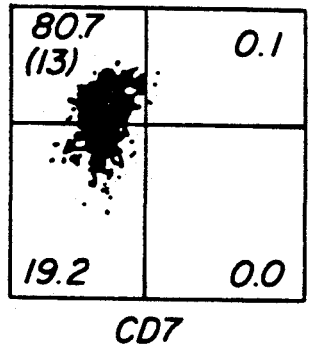
Figure 13H:
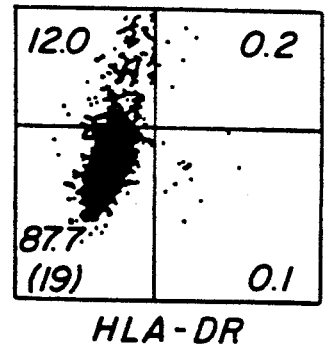

The following numbers could be assigned to the sample illustrated in FIG. 13 by examination of the quadrant statistics: 3 to FIG. 13d (greater than 30% did not express CD19 and CD10); 7 to FIG. 13e (greater than 30% did not express CD5 and CD20); 11 to FIG. 13f (greater than 30% lacked CD3 and CD22); 13 to FIG. 13g (greater than 30% lacked CD3 and not express CD7); 19 to FIG. 13h (greater than 30% lacked both CD13 and HLA-DR). The assignment of the lineage is obtained after the fourth number (i.e., 3, 7, 11, 13, 19) and assigns myeloid lineage to the acute leukemia. The number 19 gives additional information on the antigenic profile of this sample.

To illustrate some of the patterns that can be observed in the lineage assignment process of leukemias, other data was analyzed obtained from bone marrow or peripheral blood samples of an additional 60 patients diagnosed with acute leukemia. The numbers assigned to each of these patients are presented consecutively in Table 3. The numbers in parentheses in Table 3 indicate that greater than 20% of the lymphocytes in the light scatter gate are residual normal T lymphocytes. When the criteria for lineage assignment were met, the corresponding quadrant numbers were noted on a worksheet like the one in FIG. 14. The underscored numbers in the table indicate the point at which the criteria for lineage assignment were met. Lineage characterization was assigned according to the criteria in Table 2. Aberrant antigen expression also is indicated in Table 3.

TABLE 3

| Patient # | Assigned #s | Lineage |
| --- | --- | --- |
| B01004 | 1, 2, (5), 7, 9, (12), (13), (16), 18*, 19 | B-Lymphoid |
| B01011 | 1, 2, 7, 9, 15, 20 | B-lymphoid |
| B01033 | 1, 7, 9, 13*, 15, 20 | B-lymphoid |
| B01041 | 1, 7, 9, 15, 18*, 20 | B-lymphoid |
| B01035 | 1, 7, 9, 15, 20 | B-lymphoid |
| B01023 | 1, 7, 11, 15, 20 | B-lymphoid |
| B01001 | 2, 3, (5), 7, 8, 9, (12), 15, 19, 20 | B-lymphoid |
| B01027 | 2, 3, 8, 9, (12), 15, (16), 19, 20 | B-lymphoid |
| B01034 | 2, 7, 8, 9, 11, 15, 20 | B-lymphoid |
| AL05 | 2, 7, 8, 9, 13*, 15, 20 | B-lymphoid |
| AL01 | 2, 7, 8, 9, 15, 20 | B-lymphoid |
| AL02 | 2, 7, 8, 9, 15, 20 | B-lymphoid |
| B01009 | 2, 7, 8, 9, 15, 20 | B-lymphoid |
| B01013 | 2, 7, 8, 9, 15, 20 | B-lymphoid |
| B01020 | 2, 7, 8, 9, 15, 20 | B-lymphoid |
| B01021 | 2, 7, 8, 9, 15, 20 | B-lymphoid |
| B01022 | 2, 7, 8, 9, 15, 20 | B-lymphoid |
| B01024 | 2, 7, 8, 9, 15, 20 | B-lymphoid |
| B01031 | 2, 7, 8, 9, 15, 20 | B-lymphoid |
| B01032 | 2, 7, 8, 9, 15, 20 | B-lymphoid |
| B01043 | 2, 7, 8, 9, 13*, 15, 18*, 20 | B-lymphoid |
| AL03 | 2, 7, 9, 13*, 15, 20 | B-lymphoid |
| B01012 | 2, 7, 9, 13*, 15, 20 | B-lymphoid |
| B01008 | 2, 7, 9, 15, 18*, 20 | B-lymphoid |
| B01037 | 2, 7, 9, 15, 18*, 20 | B-lymphoid |
| B01042 | 2, 7, 9, 15, 18*, 20 | B-lymphoid |
| AL04 | 2, 7, 9, 15, 20 | B-lymphoid |
| B01014 | 2, 7, 9, 15, 20 | B-lymphoid |
| B01006 | 2, 7, 9, 15, 20 | B-lymphoid |
| B01019 | 2, 7, 9, 15, 20 | B-lymphoid |
| B01025 | 2, 7, 9, 15, 20 | B-lymphoid |
| B01029 | 2, 7, 9, 15, 20 | B-lymphoid |
| B01045 | 2, 7, 9, 15, 20 | B-lymphoid |
| B01046 | 2, 7, 9, 15, 20 | B-lymphoid |
| B01003 | 2, 8, 9, 15, 20 | B-lymphoid |
| B01016 | 2, 8, 9, 15, 20 | B-lymphoid |
| B01026 | 2, 8, 9, 15, 20 | B-lymphoid |
| B01040 | 2, 8, 9, 15, 20 | B-lymphoid |
| B01044 | 2, 8, 9, 15, 20 | B-lymphoid |
| AM010 | 3, (5), 7, 11, (12), 13, (16), 19, 20 | Myeloid |
| AM07 | 3, (5), 7, 11, (12) 15, (16), 18, 19, 20 | Myeloid |
| B01015 | 3, 5, 11, 15, 16 | T-lymphoid |
| B01002 | 3, 5, 12, 16, 20 | T-lymphoid |
| B01028 | 3, 5, 12, 16, 19 | T-lymphoid |
| AL013 | 3, 7, 11, 13, 17 | Myeloid |
| AM011 | 3, 7, 11, 13, 17 | Myeloid |
| AL012 | 3, 7, 11, 13, 17, 18 | Myeloid |
| AL014 | 3, 7, 11, 13, 17, 18 | Myeloid |
| AM012 | 3, 7, 11, 13, 17, 18 | Myeloid |
| AL06 | 3, 7, 11, 13, 17, 19 | Myeloid |
| AL09 | 3, 7, 11, 13, 18 | Myeloid |
| AM09 | 3, 7, 11, 13, 18 | Myeloid |
| B01017 | 3, 7, 11, 13, 18, 20 | Myeloid |
| B01030 | 3, 7, 11, 13, 18, 20 | Myeloid |
| B01007 | 3, 7, 11, 13, 19 | Myeloid |
| AL08 | 3, 7, 11, 13, 20 | Myeloid |
| AL011 | 3, 7, 11, 13, 20 | Myeloid |
| B01018 | 3, 7, 11, 13, 20 | Myeloid |
| AM08 | 3, 7, 11, 13, 20 | Myeloid |
| AL015 | 3, 7, 11, 14*, 18, 20 | Myeloid |
| B01036 | 3, 7, 11, 15, 17 | Myeloid |
| B01038 | 3, 7, 11, 15, 18 | Myeloid |

Having identified the leukemia, the combination of antibodies used to identify the leukemia can be used to monitor therapy and treatment. For example, changes in the percentage of cells in one or more of the quadrants identified in the patient analysis is an indication of a change is the cellular makeup of the patient. A decrease in the percentage is an indication of positive response to therapy. Monitoring can be performed on an as needed basis.

The following references have been cited in the specification as examples of related background information:

1. Bennett, Catovsky D, Daniel M-T. Classification of acute myeloid leukemia: A report of the French-American-British Cooperative Group. Ann Intern Med. 1985; 103:620–624.
2. Second MIC cooperative study group: Morphologic, immunologic, and cytogenetic (MIC) working classification of the acute myeloid leukaemias. Brit J Haemat. 1988;68:487–494.
3. Foon K, Todd R. Immunologic classification of leukemia and lymphoma. Blood. 1986; 68:1–31.
4. Neame P, Soamboonsrup P, Browman G. Classifying acute leukemia by immunophenotyping: A combined FAB immunologic classification of AML. Blood. 1986; 68:1355–1362.
5. Drexler H. Classification of acute myeloid leukemias P a comparison of FAB and immunophenotyping. Leukemia. 1987; 1:697–705.
6. Ryan D, Kossover S, Mitchell S, Frantz C, Hennessy L, Cohen H. Subpopulations of common acute lymphoblastic leukemia antigen-positive lymphoid cells in normal bone marrow identified by hematopoietic differentiation antigens. Blood. 1986; 68:417–425.
7. Terstappen L, Loken M. Myeloid cell differentiation in normal bone marrow and acute myeloid leukemia assessed by multi-dimensional flow cytometry. Anal Cell Pathol. 1990; 2:229–240.
8. Terstappen L, Safford M, Loken M. Flow cytometric analysis of human bone marrow. Leukemia. 1990; 4:657–663.
9. Terstappen L, Huang S, Picker L. Flow cytometric assessment of human T cell differentiation in thymus and bone marrow. In Press.
10. Terstappen L, Johnsen S, Segers-Nolten I, Loken M. Identification and characterization of normal human Plasma cells by high resolution flow cytometry. Blood. 1990; 76:1739–1747.
11. Loken M, Shah V, Dattilio K, Civin C. Flow cytometric analysis of human bone marrow: I. Normal erythroid development. Blood. 1987; 69:255–263.
12. Loken M, Shah V, Dattilio K, Civin C. Flow cytometric analysis of human bone marrow: II. Normal B lymphocyte development. Blood. 1987; 70:1316–1324.
13. Greaves M, Chan L, Furley A, Watt S, Molgaard H. Lineage promiscuity in hematopoietic differentiation and leukemia. Blood. 1986; 67:1–11.
14. Roberts G, Badawi S, Sackey K, Spence D, Sheth K, Aur R. Lineage ambiguity in acute leukemia. Cancer. 1986; 58:1473–1478.
15. Hurwitz C, Loken M, Graham M. Asynchronous antigen expression in B lineage acute lymphoblastic leukemia. Blood. 1988; 72:299–307.
16. Terstappen L, Safford M, Knemann S, et al. Flow cytometric characterization of acute myeloid leukemias. Part II. Phenotypic heterogeneity at diagnosis. Leukemia. In Press;
17. Terstappen L, Knemann S, Safford M. Flow cytometric characterization of acute myeloid leukemia. Part I. Significance of light scattering properties. Leukemia. In Press;
18. Terstappen L, Hollander Z, Meiners H, Loken M. Quantitative comparison of myeloid antigens on five lineages of mature peripheral blood cells. J Leuk Biol. 1990; 48:138–148.
19. Shah V, Safford M, Terstappen L, Loken M. Quantitative comparison of myeloid antigens on peripheral blood lymphocytes, monocytes, neutrophils, eosinophils, and basophils. In: Knapp W, Dorken B, Gilks W, et al., ed. Leucocyte Typing IV: White Cell Differentiation Antigens. Oxford: Oxford University Press; 1989:855–858.
20. Slockbower J, Belgeri K, Bruck E, et al. Procedures for the collection of diagnostic blood specimens by venipuncture. Villanova: National Committee for Clinical Laboratory Standards, 1984.
21. Clark E, Einfeld D. Human B cell surface molecules defined by an international workshop panel of monoclonal antibodies. In: Reinherz E, Haynes B, Nadler L, Bernstein I, ed. Leukocyte Typing II. New York: Springer-Verlag New York Inc.; 1986:159.
22. Nadler L. B cell/leukemia panel workshop: summary and comments. In: Reinherz E, Haynes B, Nadler L, Bernstein I, ed. Leukocyte Typing II. New York: Springer-Verlag New York Inc.; 1986:15–24.
23. Ling N, Maclennan I, Mason D. B-cell and plasma cell antigens: new and previously defined clusters. In: McMichael A, ed. Leucocyte Typing III. Oxford: Oxford University Press; 1987:302–335.
24. Haynes B. Summary of T cell studies performed during the second international workshop and conference on human leukocyte differentiation antigens. In: Reinherz E, Haynes B, Nadler L, Bernstein I, ed. Leukocyte Typing II. New York: Springer-Verlag New York Inc.; 1986:25.
25. Koller U, Peschel C. Cluster report: CD33. In: Knapp W, Dorken B, Gilks W, et al., ed. Leucocyte Typing IV. Oxford: Oxford University Press; 1989:812–813.
26. Terstappen L, Hollander Z, Meiners H, Loken M. Quantitative comparison of myeloid antigens on five lineages of mature peripheral blood cells. J Leukocyte Biol. 1990; 48:138–148.
27. LeBien T, McCormack R. The common acute lymphoblastic leukemia antigen (CD10): Emancipation from a functional enigma. Blood. 1989; 73:625–635.
28. Mayer R, Logtenberg T, Strauchen J. CD5 and immunoglobulin V gene expression in B cell lymphomas and chronic lymphocytic leukemia. Blood. 1990; 75:1518–1524.
29. Terstappen L, de Grooth B, van Berkel W, ten Napel C, Greve J. Flow cytometric characterization of chronic lymphocyte leukemias using orthogonal light scattering and quantitative immunofluorescence. Blut. 1988; 56:201–208.
30. Janossy G, Campana D. The pathophysiological basis of immunodiagnosis in acute lymphoblastic leukemia. Cancer Rev. 1988; 8:91–122.
31. Janossy G, Coustan-Smith E, Campana D. The reliability of cytoplasmic CD3 and CD22 antigen expression in the immunodiagnosis of acute leukemia: A study of 500 cases. Leukemia. 1989; 3:170–181.
32. Pui C-H, Behm F, Singh B. Myeloid-associated antigen expression lacks prognostic value in childhood acute lymphoblastic leukemia treated with intensive multiagent chemotherapy. Blood. 1990; 75:198–202.
33. Griffin J. The use of monoclonal antibodies in the characterization of myeloid leukemias. Hematol Pathol. 1987; 1:81–91.
34. Dorken B, Moller P, Pezzutto A, Schwartz-Albiez R, Moldenhauer G. B-cell antigens: CD10. In:

Knapp W, Dorken B, Gilks W, et al., ed. Leucocyte Typing IV. Oxford: Oxford University Press; 1989:33-34.

35. Dorken P, Moller P, Pezzutto A, Schwartz-Albiez, Moldenhauer G. B-cell antigens: CD20. In: Knapp W, B D, Gilks W, et al., ed. Leucocyte Typing IV. Oxford: Oxford University Press; 1989:46-48.

36. Kurrle R. Cluster report: CD3. In: Knapp W, B D, Gilks W, et al., ed. Leucocyte Typing IV. Oxford: Oxford University Press; 1989:290-293.

37. Lanier L, Allison J, Phillips J. Correlation of cell surface antigen expression on human thymocytes by multi-color flow cytometric analysis: implications for differentiation. J Immunol. 1986; 137:25012507.

38. Dorken P, Moller P, Pezzutto A, Schwartz-Albiez, Moldenhauer G. B-cell antigens: CD19. In: Knapp W, B D, Gilks W, et al., ed. Leucocyte Typing IV. Oxford: Oxford University Press; 1989:34-36.

39. Gadol N, Peacock M, Ault K. Antigenic phenotype and functional characterization of human tonsil B cells. Blood. 1988; 71:1048-1055.

40. Dorken P, Moller P, Pezzutto A, Schwartz-Albiez, Moldenhauer G. B-cell antigens: CD22. In: Knapp W, B D, Gilks W, et al., ed. Leucocyte Typing IV. Oxford: Oxford University Press; 1989:63-64.

41. Visser L, Shaw A, Slupsky J, Vos H, Poppema S. Monoclonal antibodies reactive with hairy cell leukemia. Blood. 1989; 74:320-325.

42. Andrews R, Singer J, Bernstein I. Precursors of colony-forming cells in humans can be distinguished from colony-forming cells by expression of the CD33 and CD34 antigens and light scattering properties. J Exp Med. 1989; 169:1721-1731.

43. Greaves M, Hariri G, Newman R, Sutherland D, Ritter M, Ritz J. Selective expression of the common acute lymphoblastic leukemia (gp100) antigen on immature lymphoid cells and their malignant counterparts. Blood. 1983; 61:628-639.

44. Gadd S. Cluster report: CD13. In: Knapp W, Dorken B, Gilks W, et al., ed. Leucocyte Typing IV. Oxford: Oxford University Press; 1989:782-784.

45. Bauer S, Alpert L, DiSalvo A, et al. Protection of laboratory workers from infectious disease transmitted by blood, body fluids, and tissue. Villanova: National Committee for Clinical Laboratory Standards, 1989.

46. Lal R, Edison L, Chused T. Fixation and long-term storage of human lymphocytes for surface marker analysis by flow cytometry. Cytometry. 1988; 9:213-219.

47. Terstappen L, Meiners H, Loken M. A rapid sample preparation technique for flow cytometric analysis of immunofluorescence allowing absolute enumeration of cell subpopulations. J Immunol Meth. 1989; 123:103-112.

48. Loken M, Brosnan J, Bach B, Ault K. Establishing Optimal Lymphocyte Gates for Immunophenotyping by Flow Cytometry. Cytometry. 1990; 11:453-459.

49. Hultin L, Hultin P, Kaul K, Hausner M, Cai J, Giorgi J. Dim CD20 Cells: B or T? Cytometry 1990; 109:21.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

I claim:

1. A method for classifying white blood cells in a patient sample as to leukemic type comprising the steps of:
   (a) dividing the sample into more than one aliquot;
   (b) mixing each aliquot with first and second monoclonal antibodies each labelled with a fluorochrome having distinguishable emission spectra wherein the antibodies are different and are selected from the group consisting of anti-B lymphocyte, anti-T lymphocyte, anti-monocyte anti HLA-DR, CD34 and CD38 monoclonal antibodies and each aliquot is mixed with different antibodies;
   (c) analyzing the cells in each aliquot for light scatter and fluorescence by means of flow cytometry;
   (d) constructing a bivariate plot of fluorochrome emissions for each aliquot;
   (e) dividing each plot into quadrants so that the quadrants contain first antibody single positive, double positive, second antibody single positive and double negative cells;
   (f) plotting fluorescence emissions for the cells in each aliquot, such that each cell falls into a specific quadrant;
   (g) consecutively numbering each quadrant beginning with the first antibody single positive quadrant in the first aliquot and proceeding sequentially through the double positive, second antibody single positive and double negative quadrants and then likewise through the remaining aliquots;
   (h) assigning to each aliquot one or more quadrant numbers for the quadrant wherein the percentage of cells in that quadrant exceeds a known number; and
   (i) comparing the quadrants assigned to the aliquots from the sample with a known set of quadrant numbers for each type of leukemia being examined.

2. The method of claim 1 wherein the leukemias are acute leukemias.

3. The method of claim 1 wherein the sample of cells comprises mononuclear cells separated from peripheral blood.

4. The method of claim 1 wherein the sample of cells comprises mononuclear cells separated from bone marrow.

5. The method of claim 1 wherein the number of antibodies per aliquot is three.

6. The method of claim 1 wherein the anti-B lymphocyte antibodies are selected from the group consisting of CD10, CD19, CD20, CD21, CD22, CD24, CD26, CD35, CD37, CD39, CD40, CD72, CD75, CD76 and CD79 antibodies.

7. The method of claim 1 wherein the anti-T lymphocyte antibodies are selected from the group consisting of CD1, CD2, CD3, CD4, CD5, CD6 CD7, CD8 and CD27 antibodies.

8. The method of claim 1 wherein the anti-monocyte antibodies are selected from the group consisting of CD33, CD11b, CD11c, CD13, CD14, CD15, CD16, CD48, CD63, CD64, CD65, CD66, CD67 and CD68 antibodies.

9. The method of claim 1 wherein the sample is divided into 5 aliquots and said first and second antibodies are in pairs selected from the group consisting of anti- CD10/anti-CD19; anti-CD20/anti-CD5; anti-CD3/anti-CD22; anti-CD7/anti-CD33; and anti-HLA-DR/anti-CD13.

10. The method of claim 9 wherein an additional aliquot is mixed with the following antibody pair: anti-CD34/anti-CD38.

11. The method of claim 1 wherein the fluorochromes are selected from the group consisting of fluorescein isothiocyanate, R-phycoerythrin and perdinin chlorophyll complex.

12. The method of claim 9 wherein each of the first members of the pair are labelled directly with fluorescein isothiocyanate and the second members of each pair are labelled directly with R-phycoerythrin.

13. The method of claim 1 wherein the step of dividing plots into quadrants is carried out by utilizing fluorescently labelled IgG control antibodies to define the limits of non-specific staining of the cells in the sample.

14. The method of claim 13 wherein the step further comprises utilizing unlabelled irrelevant control antibodies.

15. The method of claim 1 wherein a third monoclonal antibody is added to each aliquot and there are more than four quadrants per plot.

* * * * *